(12) United States Patent
Moularat et al.

(10) Patent No.: US 9,725,751 B2
(45) Date of Patent: Aug. 8, 2017

(54) DEVELOPMENT OF A DETECTION MICROSYSTEM

(71) Applicant: CENTRE SCIENTIFIQUE ET TECHNIQUE DU BATIMENT, Champs sur Marne Cedex (FR)

(72) Inventors: Stéphane Moularat, Lognes (FR); Yael Joblin, Sucy-en-Brie (FR); Enric Robine, Lagny-sur-Marne (FR)

(73) Assignee: CENTRE SCIENTIFIQUE ET TECHNIQUE DU BATIMENT, Champs sur Marne (FR)

( * ) Notice: Subject to any disclaimer, the term of this patent is extended or adjusted under 35 U.S.C. 154(b) by 533 days.

(21) Appl. No.: 13/729,910

(22) Filed: Dec. 28, 2012

(65) Prior Publication Data
US 2013/0171687 A1  Jul. 4, 2013

(30) Foreign Application Priority Data
Dec. 28, 2011 (FR) ...................... 11 04126

(51) Int. Cl.
C12Q 1/04 (2006.01)
G01N 33/00 (2006.01)

(52) U.S. Cl.
CPC ........... *C12Q 1/04* (2013.01); *G01N 33/0029* (2013.01); *G01N 33/0047* (2013.01)

(58) Field of Classification Search
CPC ... G01N 33/0029; G01N 33/0047; C12Q 1/04
USPC ............................. 422/83, 89; 435/34, 287.7
See application file for complete search history.

(56) References Cited

U.S. PATENT DOCUMENTS
2004/0014143 A1 * 1/2004 Haskins et al. ............... 435/7.1

FOREIGN PATENT DOCUMENTS
WO   9947905 A2   9/1999
WO   2008125770 A1   10/2008

OTHER PUBLICATIONS

"Conductive polymer-coated fabrics for chemical sensing," Collins et al, Synthetic Metals, vol. 78, Issue 2, Mar. 30, 1996, pp. 93-101.*
Enrico Cozzani: "Modeling, Design and Experimental Characterization of Micro-Electro-Mechnical Systems for Gas-Chromatographic Applications", Alma Mater Studiorum Universita Di Bologna, Mar. 6, 2011; pp. 1-125. (Scanned and sent to USPTO in 2 Parts—XPOO7920889 I & II).

(Continued)

*Primary Examiner* — Shogo Sasaki
(74) *Attorney, Agent, or Firm* — Amster, Rothstein & Ebenstein LLP

(57) ABSTRACT

This invention relates to a device for detecting fungal contamination in an interior environment, including:
  a concentration module (MC);
  a separation module (MS) including a chromatographic microcolumn; and
  a detection module (MD),
characterized in that it includes at least one first solenoid valve (E3) upstream of the detection module (MD) enabling either to direct a flow containing target molecules toward the detection module (MD), or to direct a flow filtered by a first means for filtering (Tx1), enabling the detection module (MD) to be cleaned when the flow does not contain the target molecules. The invention also relates to a control interface of the device.

10 Claims, 11 Drawing Sheets

(56) References Cited

OTHER PUBLICATIONS

Anna Capagnoli et al: "Use of the Electronic Nose as a Screening Tool for the Recognition of Durum Wheat Naturally Contaminated by Deoxynivalenol: A Preliminary Approach", Sensors, vol. 11, No. 5, Jan. 1, 2011, pp. 4899-4916.
French International Search Report for French Application No. 1104126 dated Jul. 31, 2012.
French International Written Opinion for French Application 1104126.

* cited by examiner

DEVELOPMENT OF A DETECTION MICROSYSTEM

TECHNICAL FIELD OF THE INVENTION

This invention relates to a device for detecting fungal contamination in an interior environment, the use thereof as well as a process for detecting fungal contamination in an interior environment implementing such a device.

Individuals in industrialized countries spend more than 90% of their time in closed spaces where they are exposed to numerous physical, chemical and biological pollutants. Aware of the health risks potentially caused by this complex pollution, public authorities have introduced, in the Grenelle 2 environmental code, the principle of monitoring air quality in interior environments. This principle includes the implementation of systems for measuring and providing information in establishments receiving vulnerable people (children, elderly people, etc.), and in places open to the public (schools, public transport, museums, etc.). Thus, as noted by the World Health Organization (WHO) in its report published in 2009 "WHO guidelines for indoor air quality: dampness and mould", mold is capable of causing allergies, infections, poisoning or irritation. Aside from their health impact, these microorganisms may act on the actual structure of buildings, permanently damaging structural and decorative features, a phenomenon widely feared by heritage conservationists.

The issue of these microorganisms is exacerbated by the observation that many dwellings in industrialized countries have moisture and/or mold problems. Thus, studies based on questionnaires or visual inspections show a very high proportion of contaminated dwellings. European studies thus report that the proportion of dwellings having visible mold may reach 25% (Brunekreef, 1992; Pirhonen, 1996). Studies conducted in North America show a contamination rate ranging from 14 to 38% (Dales, 1991). This proportion reaches 80% when dwellings with high moisture detected in the walls are taken into account (Miller, 1988; Koskinen, 1999).

In France, the public authorities subsidize an internal air quality observatory (Observatoire de la Quanté de l'Air Intérieur (OQAI)) managed by the Scientific and Technical Center for Building (Centre Scientifique et Technique du Bâtiment (CSTB)). The results of the national housing campaign conducted by the OQAI, published at the end of 2007, make up the first report on air quality of French dwellings. This measurement campaign shows in particular that the contamination of dwellings by mold concerns a large proportion of French homes with values of between 37 and 42%, of which 2% (i.e. more than 610,000 dwellings) had contaminated surface areas of more than 1 $m^2$ (Moularat, 2008).

Among the biocontaminants in these environments, microfungi (mold) represent a research focus for numerous teams around the world (North America, Northern European countries, Belgium, Italy, Australia, France, etc.).

By interior environment, we mean a space confined inside a building that is not continuously aerated. Examples of interior environments can be found in dwellings, museums, churches, caves, historic monuments, administrative buildings, schools and hospitals.

The presence of mold in interior environments is not without health consequences. Indeed, numerous studies have demonstrated the appearance of symptoms in occupants of buildings with mold, and also their role in the degradation both of materials and of the structures that they colonize. Indeed, the enzymes and/or the acids produced by fungi also cause the deterioration of their substrate.

Fungi, from the very beginning of their development, emit volatile molecules (volatile organic compounds, VOC) resulting either from their metabolism or from the degradation of the material on which they develop by the enzymes or the acids that they produce. VOCs spread through the walls and can be detected in the air itself in the case of hidden contaminations. However, VOCs present in an interior environment can also come from other sources such as construction materials, household products or human activity. Concentrations of VOCs of fungal origin, in particular at an early contamination stage, are relatively low compared to all of the VOCs present in an interior environment.

PRIOR ART

In this context, the applicant has spent more than ten years performing various research activities in particular on controlling the development of mold on substrates and on the early detection of the growth of same.

Traditionally, fungal contamination of an environment has been detected by visual examination or by culture of microorganisms present in the air, on surfaces or in dust. Therefore, the usual methods rarely make it possible to detect hidden contaminations (growth behind a partition, in the building structure or in ventilation systems, for example) or recent contaminations, of which no signs of development are yet apparent.

With a view to early detection of fungal development, the applicant's work is based on the emission, from the first hours of fungal development, of specific microbial volatile organic compounds (MVOC), which spread in the environment and constitute a biochemical impression, the detection of which signals fungal activity.

Thus, to detect all cases of contamination, a technique based on identifying chemical tracers comprising this impression and enabling a contamination index to be calculated has been developed by the applicant in the patent application FR 2913501.

Patent application FR 2913501 proposes a process for detecting fungal contamination in an interior environment by determining a fungal contamination index based on analysis of the VOCs present in the ambient air. This process makes it possible to detect fungal development at an early stage of its development, even in the case of hidden contamination, but implements traditional analysis methods, such as gas phase chromatography coupled with a mass spectrometer. These methods require the collection of a sample to be associated with the laboratory where it will be subjected to long steps of concentration, separation and analysis. These steps for detecting fungal contamination in an interior environment require the intervention of a qualified technician and are relatively time consuming and costly. These analysis techniques do not therefore enable rapid and continuous measurement.

The solutions currently available do not therefore make it possible to satisfy the need for early detection and continuous monitoring of fungal contaminations. The general principle of the microsystem according to the invention is described in patent application no. 10 59636.

The applicant company has managed to develop a device for detecting fungal contamination in an interior environment enabling rapid in situ analysis of the ambient air with a short measurement time, and therefore continuous detection of contamination. The device of the invention also has the advantage of being capable of being used without the intervention of a specialized technician.

PRESENTATION OF THE INVENTION

Thus this invention relates to a device for detecting fungal contamination in an interior environment, including:
- a preconcentration module;
- a separation module including a chromatographic microcolumn; and
- a detection module including a sensor matrix.

The applicant has therefore developed a self-contained system of chemical microsensors suitable for measurement in situ. In addition to the time benefit engendered by the absence of the laboratory analysis phase, integrated in the system to be developed, this device must enable continuous monitoring of environments frequented by the public, such as museums, schools, hospitals, etc.

In particular, the preconcentration module is located upstream of the other modules of the device. The use of a preconcentrator is required for the use of chromatographic systems when the resolution of the chromatographic column is too low or the sensitivity of the detectors used is limited by low concentrations of the target molecules.

Preconcentration is based on the principle of accumulation. When using a preconcentrator, the flow to be analyzed, in particular the gas, passes through the preconcentration module and the target molecules are accumulated there, during a sample collection phase, on an adsorbent material. Of course, the choice of the adsorbent material is dependent on the target modules sought, so that they can be trapped on the material, then desorbed, for example, thermally and injected into a chromatographic column so as to be separated and then analyzed. Thus, the target molecules released make it possible to obtain, at the column outlet, desorption peaks with a higher concentration of target molecules. This preconcentration module therefore increases the efficacy of the column separation and the high concentration peaks increase the sensitivity of the analysis. In the interpretation of this application, the terms "preconcentration module" and "concentration module" must be considered to be synonyms.

Preferably, the concentration module includes a preconcentration microstructure. This type of microstructure makes it possible to produce a smaller device, preferably portable and easy to handle. This type of microstructure also allows not only for lower energy consumption during desorption but also for better heating efficiency associated with a lower thermal mass an smaller dead volumes.

The presence or absence of mold in an interior environment cannot be deduced from the detection of a single fungal VOC. The present inventors have therefore designed a device that uses a principle for detection of fungal contamination based on the detection of certain target VOCs. The device of the invention therefore makes it possible in particular to detect the presence of an array of target VOCs capable of resulting from the development of fungal contamination. The target VOCs include, in particular:

(1) VOCs that are emitted independently of the fungal species and the substrate thereof, and that are emitted only by fungal species, such as 1-octen-3-ol, 1,3-octadiene and methyl-2-ethylhexanoate;

(2) VOCs that are emitted independently of the fungal species and the substrate, but that may also have other biological origins, such as 2-methylfuran, 3-methylfuran, 3-methyl-1-butanol, 2-methyl-1-butanol and α-pinene;

(3) VOCs that are emitted according to the fungal species and/or the substrate, such as 2-heptene, dimethylsulfide, 4-heptanone, 2(5H)-furanone, 3-heptanol and methoxybenzene.

Target VOCs can also include VOCs not belonging to categories (1), (2) or (3) but that are involved in the assessment of the presence of fungal contamination, such as 2-ethylhexanol.

In particular, the preconcentration module of the device according to the invention enables a concentration of target VOCs present in the ambient air up to a concentration detectable by the detection module. The VOC concentration can be obtained by any method known to a person skilled in the art, in particular accumulation on an adsorbent material. The preconcentration module therefore advantageously includes an adsorbent material enabling the accumulation of target VOCs. The structure of the adsorbent material typically has a shape enabling its specific surface to be optimized. Preferably, the adsorbent material is in the form of particles typically having a size of 50 to 200 µm, a specific surface of 20 to 50 $m^2/g$, a porosity of 1 to 5 $cm^3/g$ and an average pore size of 50 to 500 nm. The adsorbent material is preferably chosen from active carbon, silica gel, zeolites and porous synthetic resins, such as those sold under the trademarks Tenax®, Carbograph® or Chromosorb®. The preconcentration module advantageously also includes a heating system enabling desorption of the VOCs adsorbed on the adsorbent material.

In particular, said modules are successively downstream of one another. According to a first aspect, the device according to the invention includes flow generating means, preferably a pump and at least one first solenoid valve upstream of the detection module enabling either to direct a flow containing target molecules toward the detection module, or to direct a flow filtered by a first means for filtering enabling the detection module to be cleaned when the flow does not contain the target molecules.

Advantageously, the same flow is directed either to the detection module when it contains the target molecules or it is directed toward the first means for filtering when it does not contain the target molecules.

The determination of the presence or the absence of target molecules, in particular target VOCs, is performed preferably according to the retention times of the module for separating said target molecules. These retention times can be estimated by measurement standards. Advantageously, said first solenoid valve is placed between the separation module and the detection module.

According to another aspect, the device also includes at least one second solenoid valve upstream of the separation module enabling a flow to be directed either towards the separation module when the flow contains target molecules or when the flow is filtered by the means for filtering, or toward the outside when the flow does not contain the target molecules. Advantageously, said second solenoid valve is placed between the concentration module and the separation module.

Thus, during the retention of the target molecules, for example, in the concentration module, the separation module is not crowded by the other molecules of the sample collection. Moreover, it is possible to have a filtered flow pass successively through the concentration module and the separation module.

Preferably, the device also includes at least one third solenoid valve upstream of the concentration module enabling either to direct a sample collection flow toward the concentration module, or to direct a flow filtered by a means for filtering, enabling at least the concentration module to be cleaned. The filtered flow serves as a vector gas during the analysis.

Thus, outside of the sample collection phases, the device can be cleaned by a filtered flow.

Preferably, the same means for filtering is provided to generate a filtered air flow for cleaning the concentration module and the separation module.

According to an advantageous aspect, the first and/or the second means for filtering include an adsorbent polymer. In particular, the adsorbent polymer of the first and/or second means for filtering is capable of adsorbing volatile or semi-volatile molecules. Thus, the passage through such means for filtering enables the background noise to be reduced in the analysis of the target molecules and a cleaning of the different modules. For example, such an adsorbent material includes a porous polymer resin based on 2,6-diphenylene oxide. Means for filtering containing active carbon can also be envisaged.

Advantageously, the concentration and/or separation modules include a material capable of adsorbing or absorbing said target molecules associated with corresponding desorption means. Preferably, the material capable of adsorbing or absorbing said target molecules is an adsorbent polymer such as 2,6-diphenylene, preferably polymer grains in the case of the concentration module and a polydimethylsiloxane (PDMS) gel in the case of the separation module, and the desorption means include heating resistors provided on said concentration and/or separation modules.

According to another interesting aspect, the device also includes a control card enabling to control, preferably automatically, at least one among said solenoid valves, the elution means and in particular the heating resistors, and the flow generation means, in particular at least one pump.

Preferably, the control card is connected to the detection module so as to receive data from it. The signal processing cards of the detection and control module of the system can also be dissociated.

Advantageously, the control card and the detection module are configured so as to measure a difference in resistivity between the flow that includes the target molecules and the filtered flow. In particular, the detection module includes a so-called "Wheatstone bridge" assembly associated with an amplification assembly.

The invention also relates to a control card for a detection device as described above, configured so as to control, preferably automatically, said solenoid valves, so as to perform at least one of the following:
  either direct a flow containing target molecules toward the detection module, or direct a flow filtered by a first means for filtering enabling the detection module to be cleaned when the flow does not contain the target molecules,
  direct a flow either toward the separation module when the flow contains target molecules or when the flow is filtered by a second means for filtering, or toward the outside when the flow does not include the target molecules,
  or direct a sample collection flow toward the concentration module, or direct a flow filtered by a third means for filtering enabling to clean the concentration module when the flow does not contain the target molecules.

Preferably, the control card is configured so as to also control, preferably automatically, the flow generating means, in particular at least one pump.

Advantageously, the control card is configured to also control, preferably automatically, the elution means, in particular the heating resistors so as to desorb the target molecules.

The invention also relates to a process for detecting fungal contamination in an interior environment using a detection device including:
  a preconcentration module;
  a separation module including a chromatographic microcolumn downstream of the preconcentration module; and
  a detection module including a sensor array downstream of the separation module,
  flow generating means, preferably at least one pump,
the process including steps of:
  concentration, in which target molecules are retained in the preconcentration module, preferably for a concentration time;
  sensor cleaning, in which a filtered flow passes through at least one among the preconcentration module, the separation module or the detection module,
  analysis, in which the target molecules pass into the detection module, preferably for an analysis time.

More generally, the invention relates to a process for detecting fungal contamination in an interior environment using a detection device including:
  a preconcentration module;
  a separation module including a chromatographic microcolumn downstream of the preconcentration module; and
  a detection module including a sensor array downstream of the separation module,
  flow generating means, preferably at least one pump,
the process including at least one step of:
  sensor cleaning, in which a filtered flow passes through at least one among the preconcentration module, the separation module and the detection module.

According to an advantageous aspect, the process includes at least one inactive step (12, 13, 10) before and/or after said concentration and analysis steps, in which at least the flow generating means are inactivated, the steps of the process preferably being implemented continuously so as to detect fungal contamination in an interior environment.

Preferably, the detection process includes the steps for controlling, preferably automatically, at least one solenoid valve, so as to perform at least one of the following:
  either direct a flow containing target molecules toward the detection module, or direct a flow filtered by a first means for filtering enabling the detection module to be cleaned when the flow does not contain the target molecules,
  direct a flow either toward the separation module when the flow includes target molecules or when the flow is filtered by a second means for filtering, or toward the outside when the flow does not include the target molecules,
  or direct a sample collection flow toward the concentration module, or direct a flow filtered by a third means for filtering enabling the concentration module to be cleaned when the flow does not contain the target molecules.

Preferably, the detection process also includes steps for controlling, preferably automatically, the flow generating means, in particular the at least one pump so as to carry out said flow directions.

Advantageously, the detection process also includes steps for controlling, preferably automatically, the elution means, in particular the heating resistors, so as to desorb the target molecules.

The invention also relates to a computer program that can be loaded in the memory of a control unit, including software code portions for performing the detection process according to the invention when it is implemented by a control unit. Thus, the control card described above can, for example, include such a computer program.

The "bonding" of dielectric layers refers, for example, to one of the "bonding" techniques enabling closed cavities to be obtained, described in the book of S. Mir, Charlot (Charlot, 2002). In particular, "bonding" between plates ("water bonding") is a technique that makes it possible to weld together substrates of silicon or different materials (such as glass) to obtain 3D structures capable of forming closed cavities. The two techniques known to a person skilled in the art are, for example, anode welding and fusion welding.

According to an advantageous aspect, the device according to the invention includes polymer sensors. Indeed, chemical sensors are used for continuous measurement of organic pollutants. However, such sensors are not sensitive enough to detect the concentrations levels of VOCs emitted in a fungal development, or selective enough to differentiate these fungal VOCs from other VOCs coming from other sources such as construction or decorative materials, for example.

Preferably, the detection module includes a conductive polymer selected from the group including PEDOT-PSS, dibromine bifluorene, polypyrrole doped with octane sulfonate, polypyrrole doped with lithium perchlorate or any other derivative of polypyrrole, polythiophene or polyaniline.

According to an alternative, in the device of the invention, the preconcentration module includes a micro-preconcentrator. Such a micro-preconcentrator advantageously has an effective volume of 0.1 to 1 $cm^3$, preferably 0.1 to 0.5 $cm^3$, more preferably from 0.1 to 0.3 $cm^3$. The micro-preconcentrator consists of a substrate plate, such as a silicon plate, on the surface of which grooves are etched in which the adsorbent material is located. A second plate, made of a material identical to or different from the substrate (such as a glass plate), bonded to the surface of the etched substrate plate comprising the grooves, contains the micro-preconcentrator. The substrate plate has, for example, a surface of 2 to 20 $cm^2$. The grooves advantageously have a length of 3 to 10 cm, a width of 100 to 1000 µm, a depth of 100 to 500 µm, and a cross-section of 0.01 to 0.5 $mm^2$. The cross-section of the grooves may have various shapes such as rectangular, semi-circular or circular.

Advantageously, the preconcentration module also includes a forced circulation system enabling to force the passage of ambient air through the preconcentration module.

The separation module includes a chromatographic microcolumn advantageously having a cross-section of 0.01 to 0.25 $mm^2$. The length of the microcolumn must also be chosen so as to optimize the separation of the VOCs. It is advantageously greater than 1 m, preferably between 1 and 50 m. The choice of a long length makes it possible to improve the efficacy of the column and therefore to obtain a better separation of the VOCs. The microcolumn includes a stationary phase that a person skilled in the art will be able to select so as to optimize the separation of VOCs. It advantageously belongs to the polysiloxane family (for example, polydimethylsiloxane (PDMS)). Different stationary phases can also be used. These phases can be branched hydrocarbons, polyethylene glycols and polypropylene glycols, polyesters, poly(aryl ether sulfones) or stationary phases with specific selectivities.

The microcolumn includes, for example a substrate plate, such as a silicon plate, on the surface of which a groove is etched, in which the stationary phase is located. A second plate, made of a material identical to or different from the substrate (such as a glass plate), bonded to the surface of the etched substrate plate comprising the groove, contains the microcolumn. The substrate plate typically has a surface of 2 to 20 $cm^2$. The groove advantageously has a length of more than 1 m, preferably 1 to 50 m, a width of 100 to 500 µm, a depth of 100 to 500 µm, and a cross-section of 0.01 to 0.25 $mm^2$. The cross-section of the grooves may have various shapes such as rectangular, semi-circular or circular. The groove can be produced in different ways so as to minimize the bulk and therefore the size of the structure, for example in parallel loops (coils).

According to another embodiment of the device of the invention, the separation module also includes a system for selecting target VOCs preferably including a solenoid valve and a programmable unit enabling said solenoid valve to be controlled. This selection system is connected directly to the outlet of the microcolumn. The retention time, for a given stationary phase and microcolumn length, is specific to each VOC. Thus, by providing the retention times of each target VOC, the programmable unit can be preprogrammed so that the selection system selectively directs the eluate portions corresponding to the retention times of each target VOC toward the detection module, with the remainder of the eluate being removed from the analysis circuit. Said eluate portions can either be sent one after another to the detection module, over the course of the elution, or be stored and then sent together in the detection module.

The target VOCs, including primarily fungal VOCs, have very low concentrations compared to the total concentrations of all of the VOCs present in the ambient air. Thus, this selective separation of the target VOCs makes it possible to prevent the formation of a background noise and/or phenomena of hysteresis and/or saturation of the sensors of the detection module that would adversely affect the detection of the target VOCs.

The detection module of the device according to the invention includes an array of sensors advantageously chosen from the electrochemical sensors of the polymer type. The sensors preferably include a layer of a polymer or a mixture of polymers having an affinity with fungal VOCs.

VOCs can be classified into different families according to their chemical nature: aliphatic VOCs, alcohols, ketones, esters, ethers, aldehydes, aromatic VOCs, chlorinated VOCs, nitrogen-containing VOCs or sulfur-containing VOCs. There are chemical sensors enabling the detection of compounds having a determined functional group. Such sensors make it possible to detect and identify the presence of a VOC belonging to a determined family but do not make it possible to differentiate VOCs belonging to the same family.

In a particular embodiment, the sensor array includes sensors specific to each VOC family. In this case, the response of the sensor array makes it possible to conclude the presence or the absence of a VOC in a given eluate portion, but is not sufficient by itself to determine the nature of the VOC detected. However, the response of the sensor array makes it possible to determine the family or families to which the detected VOC belongs, and the knowledge of the retention time of the eluate portion considered makes it possible to known which target VOC may be present in said eluate portion. It is thus possible to deduce the presence or the absence of target VOCs by combining the information provided by the retention time and the sensor array.

In another embodiment, the array includes a set of sensors enabling an overall impression specific to each target VOC to be obtained. By overall impression, we mean the combination of responses of all of the sensors of the array. In this case, although each sensor of the array is not specific to a single target VOC, the combined response of a plurality of sensors makes it possible to specifically identify each target VOC. It is thus possible to deduce the presence or the absence of the target VOCs from the information provided by the sensor array.

In another embodiment, the sensor array includes sensors specific to each target VOC. In this case, the sensor array includes as many sensors as target VOCs and the response of each specific sensor makes it possible to individually conclude the presence or the absence of the target VOC to which it is specific.

Advantageously, the detection module also includes a confinement chamber containing the sensor array. This chamber enables the sensitive layers of the sensors to be confined so as to expose them only to the samples to be analyzed. Advantageously, the confinement chamber is made of a material with no or low VOC emissions under the analysis conditions, such as stainless steel or polytetrafluoroethylene (PTFE), so as to prevent contamination of the sample to be analyzed.

In a particular embodiment, the device of the invention also includes an information processing module such as the control card. It is capable of interpreting the signals emitted by each sensor and of deducing the presence or the absence of each target VOC. Preferably, the information processing module determines the presence or absence of fungal contamination. This determination can be made, for example, by calculating a fungal contamination index as defined in the patent application FR 2913501.

The traditional detection and/or identification methods implement complex equipment such as mass spectrometers, infrared spectrometers, flame ionization detectors or thermal conductivity detectors that are difficult to miniaturize. This device has the advantage of being capable of being miniaturized and of being capable of being used without the intervention of a specialized technician.

The device of the invention therefore has an advantage in terms of its size and makes it possible to considerably reduce the time interval between successive measurements and/or the response time of the measurement. The duration of a measurement with the device of the invention is typically 10 to 180 min, and preferably 30 to 120 min. Such a device therefore offers the possibility of implementing an effective strategy for monitoring fungal contaminations with a low time interval between measurements. Thus, an alert procedure can be envisaged in order to search for and treat contaminations in the earliest stages of development. Moreover, ambient air control systems, such as air handling units, can be slaved to the device of the invention in order to prevent or limit fungal development.

In particular, the present invention also relates to a process for detecting fungal contamination in an interior environment implemented by the device of the invention and including:
collection of a VOC sample in the interior environment;
separation of the VOCs collected; and
detection of the fungal VOCs present.

The process of the invention includes the collection of a sample of target molecules, preferably VOC in the interior environment. To do this, the device of the invention is arranged in the interior environment and the sample collection is performed by contact between the preconcentration module and the ambient air. The sample collection is performed by forced convention causing the passage of ambient air through the preconcentration module. The flow rate of the ambient air passing through the sample collection module is, for example, 10 to 1000 mL/min. The collection of the sample then lasts between 5 and 60 min. The collection is preferably performed by adsorption of VOCs on an adsorbent material. In this case, the process of the invention also includes a step of desorption of the VOCs adsorbed. This is performed by thermal desorption under conditions well known to a person skilled in the art.

The process of the invention also includes the separation of target molecules, in particular the VOCs collected. The separation of the VOCs collected is performed by the separation module. In particular, the VOCs collected are separated by elution on a chromatographic microcolumn. The optimum separation parameters such as the temperature of the column or the flow rate of the mobile phase, are determined according to techniques well known to a person skilled in the art according to the shape of the column, the nature of the stationary phase and the vector gas.

In one embodiment of the process according to the invention, target VOCs are selected from the VOCs collected by the separation module. This step is performed by the selection system during the elution of the sample on the chromatographic microcolumn. To do this, the following is performed. Each target VOC elutes at a different known rate for a given chromatographic system. Therefore, a given retention time is assigned to a target VOC. The selection system is programmed with these values. The selection system is then capable of selecting the portions of eluate having a retention time corresponding to the target VOCs. These eluate portions are then sent selectively to the detection module. The eluate portions not corresponding to the preprogrammed values are removed. Consequently, only the presence or absence of the target VOCs are detected by the detection module.

The remainder of eluate being removed from the analysis circuit prevents phenomena of hysteresis and/or saturation of the sensors of the detection module that might be caused by the presence of non-target VOCs that generally have a concentration much higher than that of fungal VOCs.

The target VOCs are preferably chosen from the group consisting of 1-octen-3-ol, 1,3-octadiene, methyl-2-ethylhexanoate, 2-methylfuran, 3-methylfuran, 3-methyl-1-butanol, 2-methyl-1-butanol, α-pinene, 2-heptene, dimethylsulfide, 4-heptanone, 2(5H)-furanone, 3-heptanol, methoxybenzene and 2-ethylhexanol and mixtures thereof.

Advantageously, the process of the invention also includes the determination of a fungal contamination index, for example by using the process as defined in patent application FR 2913501.

The process according to the invention is preferably used continuously. Advantageously, the duration of a measurement cycle is 10 to 180 min, and preferably 30 to 120 min.

BRIEF DESCRIPTION OF THE FIGURES

Other features, details and advantages of the invention will become clear from the following description, with reference to the appended figures, which illustrate.

For greater clarity, identical or similar elements are denoted by the same reference signs in all of the figures.

DETAILED DESCRIPTION OF EMBODIMENTS

Figure 1:
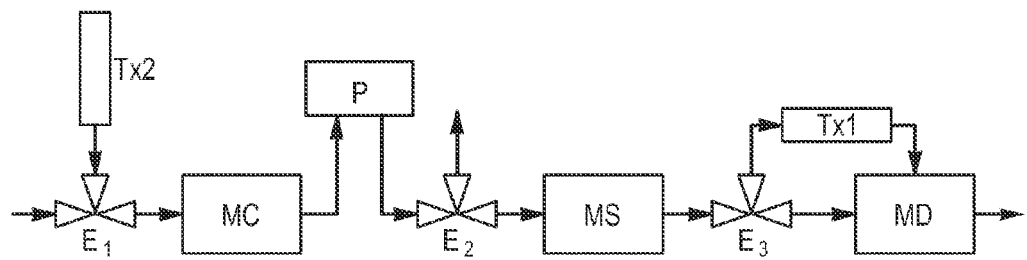
FIG. 1: a diagram of the detection device according to a preferred alternative of the invention.

In reference to FIG. 1, the device according to a preferred alternative of the invention includes a concentration module MC, a separation module MS and a detection module MD, the modules being successively downstream of one another. The device also includes a solenoid valve E1, which has two positions a and b upstream of the concentration module. This solenoid valve E1 enables the admission of an air sample when it is in position a, and the admission of filtered air through a Tenax tube Tx2 when it is in position b. The device also includes a solenoid valve E2 between the concentration module and the separation module. This solenoid valve E2 has two positions a and b and enables an orientation of an air flow coming from the concentration module MC toward the separation module MS when it is in position b, and a discharge of this flow toward the outside of the device when it is in position a. The air flows are generated by a pump P located in this case between the concentration module and the solenoid valve E2. The device also includes a solenoid valve E3 between the separation module MS and the detection module MD. This solenoid valve E3 has two positions a and b and enables an orientation of an air flow coming from the separation module MS directly toward the detection module MD when it is in position a, and an orientation of this flow toward the detection module MD by means of a Tenax tube Tx1 when it is in position b.

The following examples of embodiments show the present invention, without limiting the scope thereof in any way.

Example 1: First Embodiment of the Device

The preconcentration module includes a micro-preconcentrator etched on a silicon plate by a DRIE process. The micro-preconcentrator is comprised of 20 grooves 6 cm long, with a rectangular cross-section 500 µm wide and 250 µm long, and has an effective volume of 0.15 cm$^3$. The grooves are packed with resin particles based on 2,6-diphenyl oxide sold under the name TENAX® TA having an average diameter of 120 µm, a specific surface of 35 m$^2$/g, a porosity of 2.4 cm$^3$/g and an average pore size of 200 nm. The micro-preconcentrator is closed by a glass plate bonded to the surface comprising the grooves of the first plate.

A chromatographic microcolumn was etched on a silicon plate by a DRIE process. The microcolumn is comprised of a groove 5 m long, with a rectangular cross-section 150 µm wide and 200 µm long. The groove is produced in the form of parallel loops (or coils) having elbows in the form of an arc of circle so as to prevent the formation of dead angles. A stationary PDMS phase, polydimethylsiloxane (Sylgard® 184, sold by the Dow corning company), is present inside the microcolumn. The microcolumn is closed with a second glass plate bonded to the surface comprising the groove of the first plate.

The detection module includes a sensor array comprised of four polymer sensors. The polymer sensors have an affinity with fungal VOCs (PEDOT-PSS, polypyrrole/sodium octane sulfonate, polypyrrole/lithium perchlorate and polybifluorene, respectively) deposited on interdigital electrode pairs. The sensor array is arranged in a stainless steel confinement chamber and a PTFE seal.

The different elements are linked to one another and to the circulation system by NanoPort™ connectors.

Example 2: Calibration of the Microcolumn of the First Embodiment

For the calibration, the sensor array of the device of example 1 was replaced by a mass spectrometer.

The experimental parameters of the analysis chain are provided in table 1.

TABLE 1

| Characteristics of the GC/MS | |
|---|---|
| Parameters | Analysis conditions |
| Thermal desorber | TurboMatrix ATD (Perkin Elmer) |
| Desorption temperature | 370° C. |
| Desorption rate | 50 mL/min Nitrogen N50 |
| Desorption time | 15 min |
| Cold trap temperature (Tenax TA) | −30° C. |
| Injection temperature (40° C./s) | 300° C. |
| Transfer line temperature | 220° C. |
| Gas chromatograph/ Mass spectrometer | Autosystem XL/ TurboMass (Perkin Elmer) |

TABLE 1-continued

Characteristics of the GC/MS

| Parameters | Analysis conditions |
| --- | --- |
| Microcolumn | Sylgard 184 |
| Vector gas | Helium N60 |
| Constant pressure | 37.5 psi |
| Temperature cycle | 40° C. for 2 min |
|  | 1° C./min. to 41° C. |
|  | Plateau for 2 min |
|  | 0.3° C./min. to 44° C. |
|  | for 2 min |
|  | 1° C./min. to 47° C. |
|  | Plateau for 2 min |
| Parameters of the mass spectrometer | Quadrupole mode EI, scanning (33-400) |

Samples of the target VOCs were passed into the microcolumn to determine the retention time of each target VOC.

The retention times of each target VOC are listed in table 2.

TABLE 2

| Compounds | Retention time (min) |
| --- | --- |
| 1-octen-3-ol | 4.7 |
| 1,3-octadiene | 1.6 |
| methyl-2-ethylhexanoate | 9.1 |
| 2-ethylhexanol | 5.7 |
| α-pinene | 2.7 |
| 2-methylfuran | 0.5 |
| 3-methylfuran | 0.5 |
| 3-methyl-1-butanol | 1.4 |
| 2-methyl-1-butanol | 1.4 |
| 2-heptene | 0.8 |
| 4-heptanone | 2.1 |
| 3-heptanol | 4.8 |
| Methoxybenzene | 2.6 |

Example 3: Experimental Methods 3.1 Experimental Device for Polymer Sensors 3.1.A Data Acquisition System The experiments were conducted using a system enabling the acquisition of signals from a card comprised of conductive polymers constituting the core of the system.

The emission chambers are placed outside of the system. A filtration system comprised of a TENEX tube Tx is located upstream of the emission chamber and ensures "clean" air renewal (leakage). Downstream, a PTFE tube enables the connection between the emission chamber and a 3-way solenoid valve. All of the connections are also made of PTFE. The 3-way solenoid valve (sold by the BIO-CHEM-VALVE CORP) makes it possible to select a reference path (air filtered on activated carbon), a sampling path (emission chamber) or a cleaning path (1-butanol/water mixture).

A pump (sold by the ESCAP company) makes it possible to transfer air of different climates at 147±1 mL/min$^{-1}$ toward the sensor array confined n a PTFE chamber (internal dimensions 20×25×5 mm, i.e. a total volume of 2.5 mL).

A card adapted to this system was thus produced specifically for this study. This card consists of 12 pairs of gold electrodes (with a chromium attachment layer) deposited on a glass wafer (plate or microplate).

Polymers are then deposited between each pair of electrodes by electropolymerization or by drop-coating (deposition of a drop for the polymers in solution).

The system is controlled over time. It makes it possible to observe the change in resistivity of the sensors ($R_{sample}$), as well as to collect this data via computer so as to process it. Air filtered on activated carbon is used as a reference to determine the baseline ($R_{reference}$). A 1-butanol/water (1/50; v/v) mixture enables the complete cleaning of the sensors after exposure to an emission chamber. Indeed, this mixture makes it possible to saturate the sensor while enabling a quick return to the baseline.

The results are presented in the form of fractional differences in resistances:

$$\% \frac{dR}{R} = \frac{(R_{sample} - R_{reference})}{R_{refernce}} \times 100$$

3.1.B Deposition of Polymer Layer

Conductive polymers can be synthesized from a wide range of monomers in various solvents in the presence of a large number of counter-ions. Experiments have therefore consisted of depositing different conductive polymers, doped with different counter-ions as well as mixtures of these polymers, on the electrodes of the array of the system.

The polymers in solution were deposited by means of a micropipette cone. The polymers available in powder form were solubilized in chloroform, then deposited also by means of a micropipette cone. These polymers in solution were then doped with diiodine vapors (I2) for 2 hours. PEDOT-PSS is an already-conductive polymer in aqueous solution and therefore does not need to be doped with diiodine vapors.

The deposition of insoluble polymers is performed by electropolymerization until percolation (polymer junction between the two electrodes) by means of a 3-electrode assembly and the monomer solution (concentration of 0.05 mol·L$^{-1}$) with an electrolyte (concentration of 0.1 mol·L$^{-1}$).

Example 4: Characterization of Sensitive Layers 4.1 Differentiation of Climates by Polymer Sensors 4.1.A Characterization Based on Fungal Strains Preliminary tests, performed using different strains of the study, made it possible to obtain specific responses of polymer sensors subjected to moldy environments. All of the profiles obtained with the different strains (repeated three times) show a different behavior in the response of the sensors in a contaminated environment and a sterilized environment. As a result of this observation, a more precise characterization of the responses of polymer sensors was produced with two mold species frequently encountered in all types of interior environments: *Penicillium brevicompactum* and *Aspergillus niger*.

The experimental protocol used to characterize the responses consists of passing different air samples over the 12 polymer sensors present on the card of the system for 20 min. Among the 14 polymers and polymer mixtures tested (table 3), 5 show a different behavior of the signal according to the sample types (filtered air, control chamber, contaminated room). Tests were conducted using the following conductive polymers. The list of polymers as well as the mixtures (superposition of different layers) used to distinguish uncontaminated from contaminated environments is presented in table 3.

TABLE 3

List of conductive polymers tested.

Polymer in solution
Poly(ethylenedioxythiophene)-poly(styrenesulfonate) PEDOT-PSS
Polymers in solution doped by $I_2$

| Polymers alone | Polymer mixtures |
|---|---|
| Poly (biFluorene-EDOT-Carbazole) | PEDOT-PSS + Poly |
| Poly (4-fluorophenyl) thiophene | (biFl-EDOT-Cz) |
| (biFluorene-EDOT-Carbazole) | PEDOT-PSS + Poly |
| (COPO (biFl-EDOT-Cz) copolymer | (4-fluorophenyl) thiophene |
| Poly (EDOT-di-Cz) | PEDOT-PSS + COPO |
| Poly(3-hexylthiophene) | (biFl-EDOT-Cz) |
| (P3HT) | PEDOT-PSS + Poly (EDOT-di-Cz) |
|  | PEDOT-PSS + P3HT |

Electrodeposited polymers
Polymers alone
Polypyrrole + lithium perchlorate
Polypyrrole + sodium para-toluene sulfonate
PEDOT + lithium perchlorate The sensors having given utilizable results are based on PEDOT-PSS, polypyrrole+lithium perchlorate, PEDOT-PSS and COPO, dibromine bifluorene unit doped by diiodine vapors and Ppy/octane sulfonate (0.3 M) in ethanol and water.

The other polymers showed no response or variable non-specific responses to the stimuli applied.

A cleaning protocol enabling complete desorption of the VOCs adsorbed is preferably performed afterword to prevent this drift if these polymers are used in a sensor system dedicated to the detection of mold for in situ applications.

During the different tests, a phenomenon of dilution of the contaminated air of the chambers was also observed due to the successive sample collections. This makes it possible to explain the variations between two sample collections in the same chamber.

The VOCs emitted by the molds are polar molecules (alcohol, ketones, sulfur-containing compounds). The hypothesis put forth on the interaction mechanism would therefore be an interaction of these polar functions with the oxygen (O), sulfur (S) and nitrogen (N) atoms present on the polymers.

Example 5: Second Embodiment

In the analysis of compounds in the air, the main limits of the multi-sensor systems are their high sensitivity to moisture, drift and pollution of the sensitive layers of the sensors. However, the use of a sensor array enables quick, simple, non-invasive and non-destructive sampling for the detection and identification of volatile compounds, without a complex formation for the user being necessary.

6.1 Biological Material and Growth Substrate

The fungal species selected for these tests is a strain from the Institute of Hygiene and Epidemiology-Mycology of Brussels (IHEM): *Aspergillus niger*. This strain is preserved at 4° C. in ultrapure water on medium S10 (diluted Sabouraud agar with 2% glucose; Merck). The culture is alternated on S10, which is a nutrient-poor medium (medium closest to reality) and on oat agar, which is a nutrient-rich medium. The final culture is obtained after 7 days at 25° C. on oat agar.

Regardless of the nutrient medium, the cultures are incubated at 25° C. in the dark. This species was chosen because it is frequently found in interior environments and emits, during its development, all of the tracers of the fungal contamination index.

The growth substrate used is glass fabric to be painted. This material is cut and sterilized (121° C., 45 min, moist heat) before distilled water is added.

6.2 Specific VOC Emission Chambers

The tests on the concentration and separation modules were also conducted using 300 mL emission chambers identical to those used previously in this embodiment for the development of the contamination indices. Chemical target standards were then deposited in these chambers in order to test the different micromodules. To do this, eight compounds identified as tracers of a fungal development were used. The list of these standards (sold by the SIGMA-ALDRICH company) is described in table 4.

TABLE 4

List of standards for validation of the pretreatment modules

| Compound | Purity (%) |
|---|---|
| 2-methylfuran | 99 |
| 3-methyl-1-butanol | 99 |
| 2-methyl-1-butanol | 99 |
| 4-heptanone | 98 |
| 3-heptanol | 99 |
| methoxybenzene | 99 |
| α-pinene | 98 |
| 1-octen-3-ol | 98 |

These 8 tracers were placed in solution in ethanol in order to obtain a concentration at 5 g·L$^{-1}$.

The growth support used is glass fabric. This material is cut and sterilized (121° C., 45 min, moist heat) before distilled water is added. Each of the chambers contains 50 mL of glass beads and 5 mL of distilled water. After placing the substrate in the chambers, the load rate obtained is 7·10$^{-2}$ cm$^2$/cm$^3$.

Using these emission chambers, three climates were developed: a control climate (absence of contamination), a climate contaminated by *Aspergillus niger* and a climate containing a solution of the 8 standards. The preparation of the spore suspension used for the contamination by *Aspergillus niger* is produced by pouring 50 mL of ultrapure water on the strain subcultured on oat.

For the conditioning of the different chambers, air filtered on activated carbon (removal of the VOCs present before the start of the growth) took 30 minutes. The chambers are then placed in an oven for 7 days at 25° C. and in the dark.

6.3 Sampling and Analyses of VOCs 6.3.A Sampling of the VOCs

For the sampling and analysis of the VOCs during the phase of validation of the microstructures, two analysis chains were used. Thus, two sample collection techniques are preferred in order to enable sampling compatible with the injection system of each of the two analysis chains.

Concerning the first analysis chain, GC/MS 1 (sold by the Perkin Elmer company), the sampling is performed using a Tenax tube. As for the contamination index development part, the samplings on Tenax tube Tx are performed dynamically with a flow rate of 100 mL/min$^{-1}$ for 30 min in a chamber using an FL-1001 air pump sold by the Flec company.

Thus, the VOCs are trapped in stainless steel tubes, containing a solid adsorbent suitable for VOCs containing 4 to 18 carbon atoms, Tenax TA (sold by the Supelco company).

This adsorbent is a porous polymer based on 2,6-diphenylene oxide of which the particle size ranges from 0.18 mm to 0.25 mm (60 mesh to 80 mesh). A preliminary cleaning of the Tenax TA by thermal conditioning, under a nitrogen flow, is advantageously performed.

The Tenax tube is then desorbed with an automatic thermal desorber thus enabling the trapped VOCs to be released. The sample thus desorbed is injected directly into the column. Thermal desorption is a technique of extracting volatile organic compounds using a solid array, by heating a sample swept by an inert gas flow. The compounds are adsorbed on a cold trap at −30° C., then desorbed at 300° C. before being directed to the chromatographic column where they will be separated.

The second chain, GC/MS 2 (sold by the Hewlett Packard company), does not include a thermal desorber. In this case, the VOC sampling is performed using vials (glass flask with a volume of 2 ml), in which the gas samples to be analyzed are collected. The emissions from the chambers are then collected by an SP 725 EC membrane pump with a flow rate of 6.2 mL/min$^{-1}$ for 30 min in a chamber containing a sample collection vial.

The gas sample is then confined in the vial, then enabling the automatic injector of the analysis chain to collect an air volume by means of a syringe in one of the vials present on the auto-sampler.

6.3.B Description of the Analysis Chains

The 2 analysis chains, GC/MS 1 and 2, used to analyze the VOCs, consist of a combination of two techniques:

gas phase chromatography (GC) used to separate the VOCs;

mass spectrometry (MS) used to identify these compounds.

The characteristics of the two analysis chains, Perkin Elmer and Hewlett Packard, used to validate the microstructures, are specified in tables 5 and 6, respectively.

TABLE 5

Characteristics of the GC/MS 1 (Perkin Elmer).

| Parameters | Analysis conditions |
|---|---|
| Thermal desorber | TurboMatrix ATD (Perkin Elmer) |
| Desorption temperature | 370° C. |
| Desorption rate | 50 ml/min Nitrogen N50 |
| Desorption time | 15 min |
| Cold trap temperature (Tenax TA) | −30° C. |
| Injection temperature (40° C./s) | 300° C. |
| Transfer line temperature | 220° C. |
| Gas chromatograph/Mass spectrometer | Autosystem XL/TurboMass (Perkin Elmer) |
| Capillary column | CP-SIL PONA CB |
| geometric characteristics of the column: length, internal diameter, thickness of the stationary phase | 50 m; 0.21 mm; 0.5 μm |
| Vector gas | Helium N60 |
| Constant pressure | 37.5 psi |
| Temperature cycle | 40° C. for 2 min |
| | 1° C./min to 41° C. |
| | plateau for 2 min |
| | 0.3° C./min to 44° C. for 2 min |
| | 1° C./min to 47° C. |
| | plateau for 2 min |
| Mass spectrometer parameters | Quadrupole mode EI, scanning (33-400) |

TABLE 6

Characteristics of the GC/MS 2 (Hewlett Packard)

| Parameters | Analysis conditions |
|---|---|
| Injection temperature (40° C./s) | 300° C. |
| Transfer line temperature | 200° C. |
| Gas chromatograph/Mass spectrometer | HP 6890/HP 5973 |
| Capillary column | HP-SMSUI (phase: 5% phenyl 95% polymethylsiloxane) |
| geometric characteristics of the column: length, internal diameter, thickness of the stationary phase | 30 m; 0.25 mm; 0.25 μm |
| Vector gas/flow rate | Helium/0.5 mL/min |
| Temperature cycle | Isothermal 40° C. for 10 min |
| Interface | 200° C. |
| Mass spectrometer parameters | Quadrupole mode EI, scanning (20-700) |
| MS source temperature | 230° C. |
| MS quadrupole temperature | 150° C. |

For the 2 analysis chains, the spectra obtained are compared to a mass spectral library (NIST, 1998).

Two analysis modes were used to detect compounds:

the so-called "scanning" or "fullscan" mode, used to record so-called "source" spectra, i.e. spectra where all of the ions produced in the source at a given moment are present;

"SIM" ("Single Ion Monitoring") mode, which consists of detecting only one (or a few) ion(s). The mass spectrometer therefore functions as a filter. It is programmed to detect only a few ions characteristic of the analytes studied (1 to 4, in general). The increase in the signal associated with the detection of the analytes enables the sensitivity to be improved while reducing the chromatographic background noise. With a quadrupole, the scanning time (dwell) of the ions is proportional to the range of ratios m/z scanned. Working on few m/z values therefore considerably increases the time imparted to the detection of corresponding ions, by comparison with the "fullscan" mode. The "SIM" mode is used when low sample concentrations are injected.

Thus, in a sample collection with a Tenax tube, a split at the column outlet enables 3% of the sample volume collected, i.e. 90 mL, to be injected in order to protect the detector if there is an excessive concentration of a compound.

In a sample collection with a vial, the volume injected is 5 μL. There is therefore a dilution factor of 18,000 by comparison with an analysis of a sample collected on a Tenax tube. Table 7 lists the characteristics of the sample collection according to the two sampling modes used.

TABLE 7

Characteristics of sample collections

| | Sample collection mode | |
|---|---|---|
| | Tenax tube | Vial |
| Flow rate (mL/min$^{-1}$) | 100 | 6.2 |
| Time (min) | 30 | 30 |
| $V_{collection}$ (mL) | 3000 | 186 |
| $V_{injection}$ | 90 mL | 5 μL |

6.4 Devices for Validating Modules
6.4.A Preconcentration Module

The concentration microstructure developed in this embodiment is comprised of a silicon substrate in which grooves 60 mm long and 500 μm wide are etched. The fusion with a glass substrate enables closed cavities to be produced. The microstructure is then functionalized with Tenax grains with an average diameter of 120 μm. Fluid connectors suitable for this type of microstructure make it possible to equip the access openings of the micromodules with capillaries in order to enable the connection with a pump and to enable air to circulate through the structure.

The test protocol concerning the concentration microstructure preferably involves the use of two sample types, a sample with tracers (emission chamber containing the mixture of 8 tracers) and a sample with fungal contamination (emission chamber containing glass fabric contaminated by *Aspergillus niger*).

The test protocol consists of collecting air from the different chambers through the preconcentrator for 30 min at a flow rate of 6.2 mL/min$^{-1}$ by means of an SP 725 EC membrane pump. The sample from the preconcentrator is then desorbed at 140° C. for 30 min and extracted via the pump in a chamber containing a sample collection vial. The sample from the preconcentrator contained in the vial is then analyzed on a GC/MS analysis chain.

6.4.B Separation Module

The separation microstructure developed in this embodiment is also comprised of a silicon substrate in which a groove 5 m long, 150 μm wide and 200 μm deep, is etched. The fusion with a glass substrate enables the channel to be produced. The microstructure is then functionalized with a stationary phase comprised of PDMS so as to enable the molecules passing through it to be retained. As for the concentration microstructure, suitable fluid connectors make it possible to equip the access openings of the micromodules with capillaries in order to enable the connection with a pump and to enable air to circulate through the structure.

Once the chromatographic microcolumn has been produced and functionalized, tests were conducted in order to verify its efficacy for retaining and separating the different target compounds of the study.

For this, the gas phase chromatography analysis bench used in the development of contamination indices was used by replacing the traditional chromatographic column with the microcolumn. The mass spectrometer was used at the outlet to identify the compounds.

Two sample types were also used in the microcolumn test protocol: a sample with tracers (emission chamber containing the mixture of 8 tracers) and a sample with fungal contamination (emission chamber containing glass fabric contaminated by *Aspergillus niger*). The air samples of the different chambers are collected by means of a Tenax tube at a flow rate of 100 mL/min$^{-1}$ for 30 min by means of a pump (Air Pump 1001, Flec). The tubes are then placed in the automatic thermal desorber of the GC/MS analysis chain to enable them to be analyzed. The samples are thus separated by the microcolumn and analyzed at the outlet by mass spectrometry in order to verify the retention efficacy. In the microcolumn test protocol, the vial sample collection method was also used. The samples were also analyzed by replacing the traditional column with the microcolumn in the second GC/MS analysis chain.

Example 6: Process for Producing Pretreatment Modules

7.1.A Elements Comprising Micromodules

To define the micromodule production process, the first technological choice concerns the substrate used to etch the patterns. Silicon is a base material very widely used to produce microsystems owing to its mechanical and electrical characteristics. Monocrystalline silicon is abundant and inexpensive, and is a material well suited for miniaturization.

The devices were produced on a silicon substrate using two-sided plates (wafers) with a diameter of 4 inches (around 10 cm) and a thickness of 500 μm (between 475 and 525 μm).

The production of microfluidic structures involves being capable of producing a connection between the microsystem and the air circulation system (micropump, valve, etc.). The solution used in this embodiment is the use of a "NanoPort". These fluid connectors are suitable for microstructures and make it possible to equip the access openings of the micromodules with capillaries. The positioning of these connectors requires a good alignment between the access opening of the microstructure and the opening of the connector enabling the capillaries to be inserted. These connectors are comprised of an adhesive ring, a sealing joint, the connector body, and finally the "screw" enabling the capillary to be inserted.

The tubes used in this embodiment to produce the connections between the different modules of the system are PEEK tubes with an external diameter of 1/32 inches (800 μm) and an internal diameter of 0.008 inches (200 μm).

The use of two modules, which are a chromatographic microcolumn and a concentration microstructure, involves being capable of controlling the temperature thereof. Indeed, the temperature of a column influences its efficacy and the concentration structures require a heating temperature to be capable of releasing the trapped molecules. From this perspective, heating resistors were therefore integrated in the micromodules.

The material most often used in the literature for this type of application is platinum. In addition to a positive temperature coefficient, and a good sensitivity factor, this material has a high resistivity. A material with high resistivity has the advantage of dissipating a large amount of heat by the Joule effect. Platinum is also characterized by high temperature linearity. The use of platinum, however, requires the use of an attachment layer. The material used to produce this attachment layer is titanium. The deposit thicknesses are, respectively, for titanium and platinum, 50 and 100 nm.

7.1.B Mask Design

The use of lithography remains, in silicon technologies, a very widely used process for the production of microstructures such as chromatographic microcolumns or concentration microstructures. It makes it possible to produce high-resolution structures. The approach generally used to produce this type of structure is called "top-down", i.e. starting with the substrate, the process involves etching the pattern in the material.

Lithography involves first designing masks, used in the actual production process, enabling exposure areas and therefore etching areas of the substrate to be defined. The design of these masks was performed using Coventor 2008 software.

These masks thus make it possible to define the final shape of the structures. To produce our two "separation" and "concentration" modules, 3 mask levels were therefore necessary: the first defining the shape of the grooves etched on the front face, the second defining the shape of the grooves etched on the back face, to create structure access openings, and finally, the third to produce heating resistors also on the back side.

Microcolumn Masks

The first mask level, N1, therefore concerns the shape of the grooves, sill, of the column. A plurality of geometric shapes can be envisaged concerning the arrangement of the grooves of a microcolumn in order to limit the bulk and therefore the size of the structure. In this embodiment, the geometric shape used is a "coil"-type configuration. To limit the dead volumes and facilitate the column packing, the elbows of the column between each groove were produced in the form of an arc of circle enabling a structure not having right angles to be produced. The choice of the column length was set at 5 m. The choice of this relatively long length for this type of microstructure is based on the fact that this device must enable the separation of complex samples of different compounds. The choice of a long length thus makes it possible to improve the efficacy of the column and therefore to obtain a better separation of the compounds.

The geometric characteristics of the chip for producing the microcolumn are listed in table 8.

TABLE 8

Geometric characteristics (in μm) of the microcolumn chip

| Grooves | | | Elbows | | | Chip | |
|---|---|---|---|---|---|---|---|
| Length | Width | Space between grooves | Number of grooves | Radii of elbows | Width of elbows | Length | Width |
| 30000 | 150 | 100 | 162 | 125 | 150 | 41400 | 40900 |

As for the choice of positive or negative photosensitive resins, in a production process, the choice of the "polarity" of the mask during the mask design must be specified. Thus, the data imprinted on the mask ("digitized data") must be provided either in light with a dark background, or in dark with a light background. To produce this first mask level, the polarity was chosen with the data in light.

The second mask level, N2, concerns the access openings to the microstructure. The choice used in this embodiment is to access the structure from the back side of the substrate via NanoPorts enabling the connection between the microsystem and the air circulation system by means of a PEEK tube. As the internal diameter of the PEEK tubes chosen is 200 μm for an external diameter of 800 μm, the dimensions of the access openings used are 400 μm in diameter so as to facilitate the positioning of the NanoPort. Indeed, these dimensions enable the tube to abut on the structure and prevent a risk of overlapping of the openings of the tube and the structure. The polarity of this mask was also chosen with the data in light.

The third mask level, N3, concerns the creation of heating resistors used to heat and control the temperature of the structure. The prior art known to a person skilled in the art shows the importance of the temperature in the production of this type of separation microstructure.

The value of a resistor is dependent on these geometric characteristics since it is defined by the following formula:

$$R = \rho \frac{l}{S} = \frac{\rho}{e} \frac{l}{w}$$

wherein p is the resistivity of the material, l is the length, w is the width, S is the surface and e is the thickness.

The heating resistors can be integrated with the microstructures; nevertheless, in a first stage, a confinement chamber integrating an external heating resistor is used.

Figure 2:
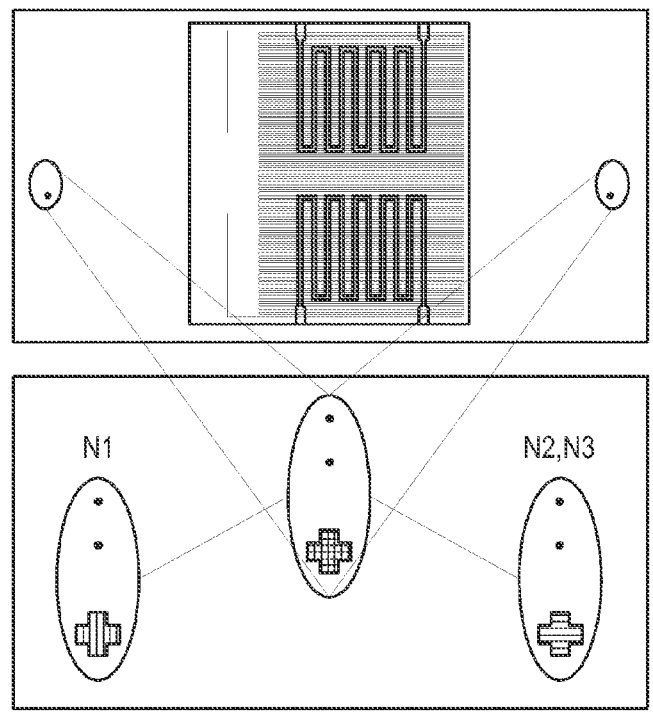
FIG. 2: a representation of alignment patterns of the pretreatment microstructure.

The presence of alignment patterns is preferable in the lithography phase in order to make it possible to superimpose the different masks and align the different patterns present on each mask. The positioning of the different masks is performed by the aligning and superimposing two geometric figures. The alignment patterns generally found and used in this embodiment are crosses (FIG. 2).

In this embodiment, the presence of alignment patterns makes it possible in particular to position the access openings, orif, on the back face, post, with the inlet/outlet openings present on the front face, ant, at the ends of the microchannels. In this case, the precision of the alignment patterns is more important if an offset of several micrometers between these two patterns can render the structure unusable. The use of small alignment patterns thus makes it possible to obtain alignment precisions on the order of 1 μm.

Alignment patterns are also present on the mask of the heating resistors RC in order to position them under the surface formed by the microchannels.

Figure 3:
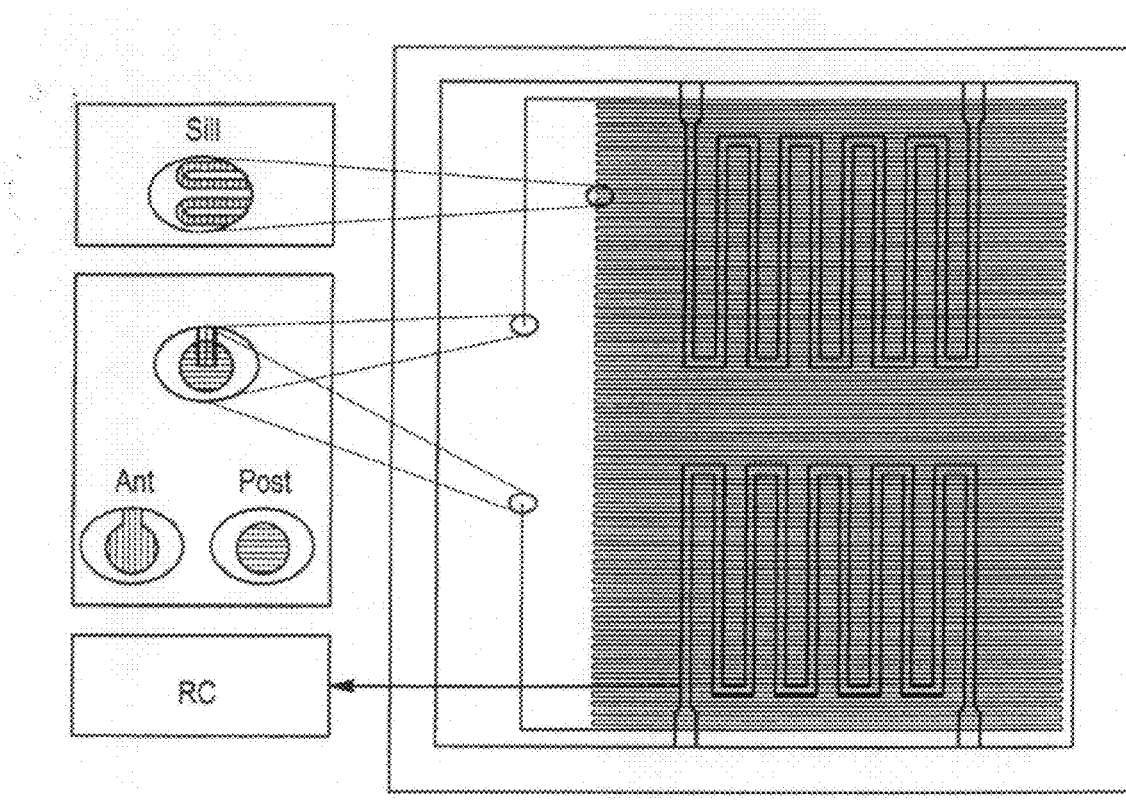
FIG. 3: a representation of the 3 mask levels for the production of a chromatographic microcolumn.

An image of the different mask levels developed with Coventor 2008 in order to produce a microcolumn chip is presented in FIG. 3.

Micro-Preconcentrator Mask

To produce the concentration microstructure, a plurality of geometric shapes can also be envisaged. The adsorbent material used in this embodiment enabling the molecules selected for fungal detection to be trapped is TENAX TA. To facilitate the packing of the structure with this material (available in grain form), a structure without any elbows was used. The TENAX sample collection tubes traditionally used for the detection of VOCs in our study contain an effective volume of 1 cm$^3$ (length of 5 cm and diameter of 0.5 cm), with grains having an average diameter of 300 μm. To produce the preconcentration microstructure, the size of the grains used is smaller (average diameter of 120 μm). The use of a smaller diameter enables the specific surface to be increased (6 times); therefore, a reduction in the effective volume to 0.25 cm$^3$ (by 4) was used. Grooves 60 mm long and 500 μm wide were thus developed.

To keep the grains in the microstructure during the passage of the air, a grid was produced using micropillars at the outlet of the structure. As the size of the TENAX grains inserted into the structure could have a minimum diameter of 75 μm, the dimensions of the grid used involved pillars 56 μm wide with a space between pillars of 55 μm.

The geometric characteristics of the chip for producing the micro-preconcentrator are reported in table 9.

TABLE 9

Geometric characteristics (in µm) of the preconcentration chip

| Grooves | | | | | Tenax grid | | Chip | |
|---|---|---|---|---|---|---|---|---|
| Length | Width | Space between grooves | Number of grooves | Pillars | Space between pillars | Length | Width |
| 60000 | 500 | 50 | 20 | 56 | 55 | 84600 | 11450 |

Concerning the access openings on the second mask level, the technological solution (NanoPorts) and the geometric characteristics of the openings used are identical to those used for the production of the microcolumn chip.

As for the design of the microcolumn masks, the integration of heating resistors with the preconcentration module is also envisaged, and a third mask level was therefore developed. However, a confinement chamber is also provided in a first stage in order to make it possible to use an external heating resistor.

Figure 4:
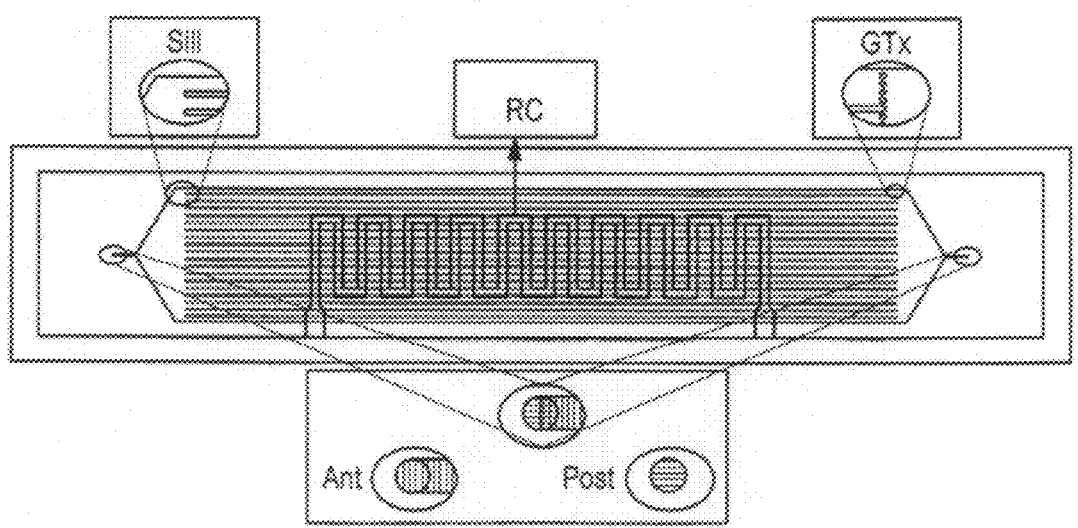
FIG. 4: a representation of the 3 mask levels for the production of a preconcentration microstructure.

An image of the different mask levels developed with Coventor 2008 in order to produce a preconcentration chip is presented in FIG. 4.

7.1.0 Process for Producing Pretreatment Modules

The production of such structures naturally presents the problem of choosing a production procedure, or more precisely an etching technique, compatible with such resolutions. The characteristic dimensions of the channels are approximately one hundred microns and the cross-sections are traditionally rectangular, semi-circular or circular. According to the bibliography, the shape of the cross-section for capillary columns does not influence the separation efficacy of the column. This observation therefore makes it possible to do eliminate constraints concerning the etching shape defined by the production process.

DRIE is a production process enabling deep anisotropic etchings with a high aspect ratio to be produced. The choice of a rectangular cross-section produced by DRIE etching was thus made.

Figure 5:
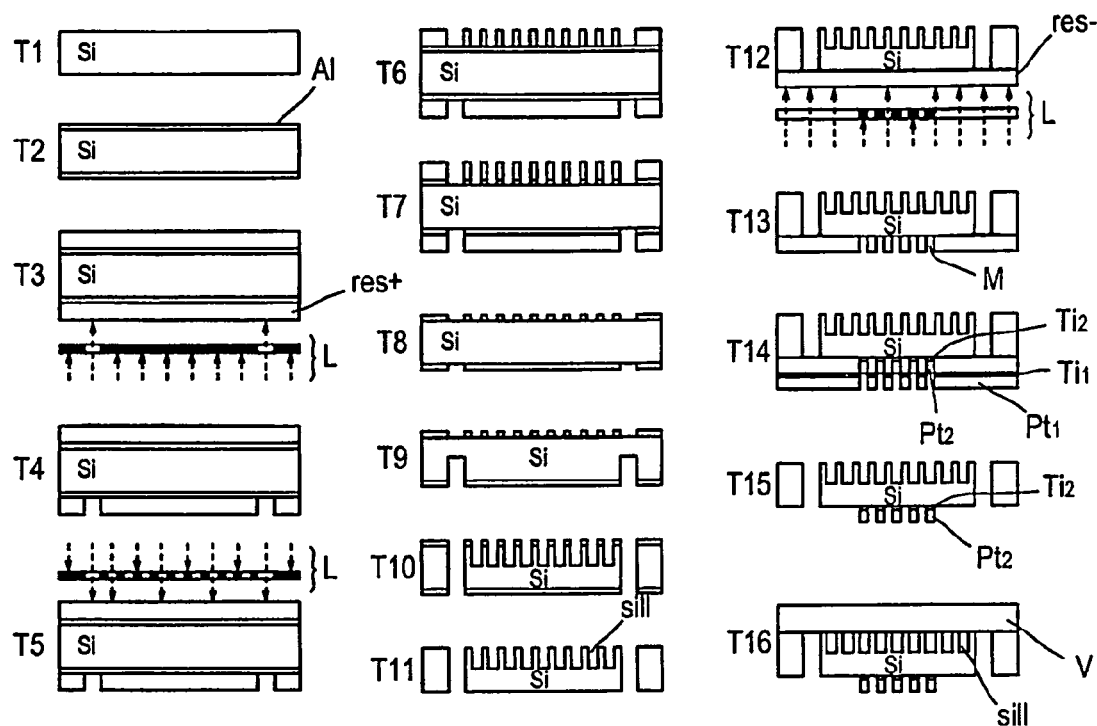
FIG. 5: a diagrammatic representation of the process for producing pretreatment micromodules.

For the two pretreatment modules of the sample, which are the microcolumn and the preconcentrator, the production process used is substantially the same and detailed in FIG. 5. The main difference in the process between the two modules concerns the etching depth of the grooves. Thus, an etching depth of 200 µm was defined for channels forming the chromatographic microcolumn and an etching depth of 250 µm was defined for the grooves of the preconcentration structure.

Step T1: Cleaning of the Wafer

The substrate (Si) of the plate (wafer) is preferably soaked in an HF 1% bath until hydrophobia is obtained. It is then rinsed in deionized water for 5 min. The cleaning consists, in a first stage, of dissolving the organic impurities using sulfuric acid ($H_2SO_4$ at 150° C. for 3 min). In a second stage, the metallic impurities are trapped by the formation of a surface oxide using nitric acid ($HNO_3$ for 3 min). The wafer is then rinsed again for 5 min in deionized water, then the oxide layer formed is removed by a new HF 1% bath, before a final rinsing with deionized water. The wafer is then dried under nitrogen.

Step T2: The Aluminum Deposition

The DRIE etching preferably involves the use of a protective layer enabling to define the areas where the substrate will not be etched. The protective layer used in this embodiment is an aluminum layer, Al, with a thickness of 5000 Å (i.e. 500 nm). The deposition is performed by cathode sputtering at ambient temperature (24° C.) in an argon plasma. The acceleration of ions is obtained by a difference in potential of 0.5 kV. The deposition is performed under low pressure, at $3 \cdot 10^{-7}$ Torr. The deposition time is dependent on the desired aluminum thickness. As the deposition rate, with this parameters, is around 1000 Å/min, the deposition lasts 5 min.

The next steps consist of defining DRIE etching areas of the wafer, i.e. areas not protected by an aluminum layer. These steps therefore comprise a traditional UV photolithography phase on each face of the wafer, then wet etching of the aluminum layer.

Steps T3, T4, T5 and T6: Definition of Etching Areas

Step T3 therefore consists of depositing, on each face of the wafer, a photosensitive resin layer, res+. In our case, the resin chosen is a positive resin (PFR 7790), i.e. the resin areas exposed to UV will be dissolved. The resin is first deposited uniformly on a face of the wafer, using a whirler. The parameters for spreading the resin (rotation speed, acceleration and in particular viscosity of the resin) determine the final thickness of the deposit. As the desired thickness is 1.2 µm, the rotation speed for the chosen resin is 4500 $rpm^{-1}$ with acceleration of 2000 $rpm^{-2}$ for 30 s. The use of a resin layer on both faces of the wafer preferably means a short annealing time for the resin (5 min at 110° C.) in order to harden it and remove some of the solvents.

The deposition of the resin on the second face of the wafer is then performed under the same conditions, followed by annealing for 15 min at 100° C.

The first photolithography step, L, on the back face can now be performed. The exposure parameters (power of the lamp and exposure time) make it possible to define the sharpness of the patterns. In our case, the exposure time is set at 10 s with a lamp power of 345 W.

Step T4 then consists of developing the resin in particular in order to cause the alignment patterns to appear so that it is possible to align the mask of the front face, during exposure. The wafer is therefore immersed in the developer bath (PRD 238) for 1 min 10 s. The wafer developed is then rinsed with deionized water for 3 min and dried.

Step T5 then consists of performing the photolithography on the front face. For this, an alignment between the patterns of the mask and those of the wafer on the back face is preferable before the exposure. The coordinates of the patterns of the wafer are stored and the position of the mask can then be aligned under the microscope with the coordinates of these patterns. Once the alignment has been performed, the conditions for exposure of the front face are the same as for those of the back face.

Step T6 consists of developing the resin in the developer bath and thus causing the patterns of the front face to appear. The wafer is immersed in the bath until the patterns fully appear.

A second annealing is finally preferable in order to heat the wafer in order to fully harden the resin. This annealing step is performed in an oven at 100° C. for 15 min. The wafer is also cleaned using an O2 plasma in order to remove the resin residue (in particular the bottoms of the etching holes) after the development and to improve the sharpness of the holes in the resin.

Step T7: Etching of the Aluminum, Al

The etching of the aluminum is performed in a chemical solution comprised of acids enabling the aluminum to be attacked ("Al etch"). The solution is kept at a temperature of 30° C. The etching is checked visually until total removal of the aluminum layer in the areas defined by the resin. The wafer is then rinsed in deionized water.

Step T8: Removal of the Resin Layer

Once the aluminum layer has been etched, the wafer is immersed in acetone in order to remove the resin layer and the wafer then moves on to the rinser. The rinser is a drum with water cleaning first rotated at 300 $rpm^{-1}$, then at 1000 $rpm^{-1}$ and heated slightly in order to dry the wafer.

Steps T9 and T10: Back Face (Lower) and Front Face (Upper) Etching

In the DRIE etching for the creation of access openings, the etching must be performed over the entire thickness of the Si substrate, one portion being etched from the front face with grooves, the other portion being etched from the back face. An over-etching from the back face (the etching depth from the front face being set by the depth of the grooves) is preferable in order to obtain a vertical wall on the entire substrate. Indeed, without this over-etching, the intersection between the etchings of each side of the substrate would be accompanied by a reduction in the diameter of the hole.

For the microcolumn chip, the etching depth of the grooves is set at 200 μm. As the substrate thickness is 500 μm, the etching depth from the back face is therefore set at 360 μm (60 μm of which consists of over-etching).

For the preconcentrator chip, the etching depth of the grooves is set at 400 μm. As the substrate thickness is 500 μm, the etching depth from the back face is therefore set at 160 μm (60 μm of which consists of over-etching).

Two types of gas are injected alternately to produce a DRIE etching, the first being SF6 for the silicon etching, injected into the chamber at 300 $mL/min^{-1}$ for 6 s, the second being C4F8 for the deposition of an inhibiting film, injected into the chamber at 150 $mL/min^{-1}$ for 2 seconds. The pressure in the chamber is between 3 and 4 Pa. Forty-five-minute etching cycles are used (in particular to prevent excessive heating of the wafer). A measurement of the etching depth after a given time makes it possible to define the etching time necessary for obtaining a desired depth. Under the conditions used, the etching rate is generally close to 5 $\mu m/min^{-1}$.

Once the DRIE etching has been completed on the back face, the DRIE etching on the front face is performed under the same conditions. The etching depths are respectively set for the microcolumn chip and the preconcentrator chip, at 200 μm and 400 μm.

Step T11: Removal of the Aluminum Layer

After the DRIE etching steps, the wafer is immersed in an acid bath enabling to remove the aluminum layers. The acid solution is kept at a temperature of 60° C., thus enabling to accelerate the process of etching the aluminum residues. The wafer is then cleaned in an oxygenated water bath ($H_2O_2$ 30%)/sulfuric acid ($H_2SO_4$) for 15 min, then under hot $O_2$ plasma (225° C.) to remove the remainder of the residues.

Steps T12, T13, T14 and T15: Production of Heating Resistors RC1 or RC2

The next steps then make it possible to produce titanium/platinum heating resistors. The process used for deposition of the resistors is a "lift-off" process, i.e. an additive technique (by contrast with the etching techniques) using a sacrificial layer.

Steps T12 and T13 constitute a traditional photolithography step, L, with the use of a negative resin, "res" (the unexposed resin is dissolved) as a sacrificial layer. The resin is therefore spread by means of a whirler in order to obtain a thickness of 7 μm. An annealing at 110° C. for 90 seconds is then performed. An alignment under microscope of the mask M containing the patterns of the resistors is performed after storing the position of the alignment patterns etched on the wafer. The resin is then exposed for 90 s before a new annealing of 90 s at 110° C. The wafer is then immersed in a developer bath (AZ351B/water) and then moves on to the rinser.

Step T14 consists of producing successive deposits of the two metal layers used to produce the resistors, i.e. 500 Å (50 nm) of titanium, Ti1, for the attachment layer and 1000 Å (100 nm) of platinum, Pt1. Before the deposition of the metal layers, the substrate is stripped with argon plasma in order to properly clean the holes produced and avoid resin residues at the bottom. The depositions of the titanium, Ti, and platinum, Pt, layers are performed under low pressure ($1 \cdot 10^{-2}$ mbar) for 1 min 15 s and 1 min 35 s, respectively, over the entire surface of the wafer reaching the substrate in the etched areas and deposited on the resin in the non-etched areas.

Step T15 then consists of removing the sacrificial layer. To do this, the wafer is immersed in an acetone bath under ultrasound. When the sacrificial layer is removed, the metal layers in contact on the resin are torn off. After removal of the sacrificial layer, the metal layers (Ti2 and Pt2) remain only in the contact areas with the substrate. The wafer is then subjected to different cleanings in order to remove the different residues (bath for the polymer residues such as resins, oxygenated water/sulfuric acid bath and HF 1%).

Step T16: Anodic Welding

The direct micromachining of the silicon makes it possible to obtain structures open to the outside (grooves, sill). Anode welding between wafers is a technique that makes it possible to weld together substrates of silicon or different materials (such as glass) in order to obtain closed cavities. The solution used to produce closed cavities is anode welding between the silicon wafer (containing grooves) and a glass wafer, v.

The anode welding is performed at a high temperature of 420° C. under vacuum ($10^{-4}$ to $10^{-5}$ mbar) and under an electric field of 500 V for 10 min.

7.1.D Microfluidic Connections

To enable the microstructures to be packed, but also to enable the circulation of air samples, they must be equipped with microfluidic connectors (NanoPorts) mentioned above.

The method for installing the connectors preferably involves, in a first stage, cleaning the wafer surface with ethanol to ensure good adhesion of the adhesive. Once the surface has been cleaned, the adhesive ring is positioned around the access opening of the microstructure. The sealing joint is then placed below the connector body in a positioning "ring". The connector body is then deposited on the adhesive ring and must be carefully positioned to enable the openings of the wafer and the connector to be aligned. The alignment is checked visually.

Once the connector has been positioned, the wafer and the connector body are held in place by a clamp thus enabling the compression of the seal and ensuring the tightness of the connection. A glass plate is first placed in contact on the other face of the wafer (glass side) to prevent direct contact between the microstructure and the clamp. The assembly is then placed in the oven at 180° C. for 2 hours.

7.2 Process for Functionalizing Modules
7.1.A Separation Microstructure

Once the microcolumns were produced and the microfluidic connections were in place, they were functionalized with their packing by a stationary phase enabling the elution and separation of the gaseous compounds.

In the analysis of the VOCs for the development of contamination indices, the separation of the different compounds was performed by gas phase chromatography using a capillary column containing PDMS (preferably 5% phenyl—95% polydimethylsiloxane) as a stationary phase. The choice of a similar column composition, with a stationary phase consisting of PDMS (polydimethylsiloxane), was made for the production of the microcolumns.

The PDMS used (Sylgard® 184, sold by the Dow corning company) is sold in the form of two liquids, the base and the crosslinking agent. The two constituents are generally mixed with a mass ratio of 10:1 (base:crosslinking agent). The crosslinking reactions begin with the mixing, thus producing a progressive increase in viscosity, followed by the formation of a gel. During mixing, air bubbles are introduced and must be removed before performing the packing in order to enable a uniform deposition over the entire length of the column. To remove the bubbles, the mixture is placed in a vacuum chamber. The removal time varies according to the amount of air introduced.

To be inserted into the micromodule and enable the production of the channel with the active substance, namely the stationary phase, the mixture is then diluted in a solvent. To obtain the best possible separation efficacy with a chromatographic column, the deposition of a homogeneous stationary phase layer is necessary. The deposition of the stationary layer can then be performed according to two methods: dynamic ("dynamic coating") or static ("static coating") packing:

- the dynamic packing procedure consists of packing a portion of the column with solution, which is then pushed through the column, at an approximate rate of 1 to 2 cm/s$^{-1}$, by inert gas pressure. A fine layer of the solution is then left on the walls of the column. After packing, the gas flow is maintained during evaporation of the solvent, thus leaving a stationary phase layer on the walls of the column. The column is heated above the boiling point of the solvent in order to remove the residual traces of solvent. The thickness of the film is defined by the proportion of solvent used for the dilution of the phase. This simple method nevertheless presents problems leading to a non-uniform deposition of the stationary phase (Xu and Vermeulen, 1988).
- the static packing procedure consists of entirely packing the column with the stationary phase solution diluted in the solvent. After packing of the column with the solution, one end of the column is plugged and the other end is connected to a vacuum pump. The column is then placed in the oven or in a double boiler in order to control the temperature of the column. The evaporation of the solvent is performed by applying a vacuum, leaving a uniform deposit of stationary phase on the walls of the column. With this procedure, the ratio between the solvent and the stationary phase is known precisely and therefore, knowing the density of the stationary phase, the thickness of the deposit can be determined precisely (Xu and Vermeulen, 1988).

The choice of a static packing was made for the functionalization of the microcolumns. The process of functionalization of the columns therefore comprises 3 steps:

Step 1: Preparation of the Solution

With the static packing process, the thickness of the stationary phase layer is dependent on the concentration of the solution and may be determined by the following equation in the case of a capillary column with a circular cross-section:

$$\frac{1}{4}\pi d_c^2 c = \pi d_c d_f$$

wherein dc is the internal diameter of the column, c is the concentration of the solution and df is the thickness of the deposited layer; thus:

$$c = 4\frac{d_f}{d_c}$$

The solvent used for the microcolumn packing is n-pentane. This solvent has the advantage of being highly volatile since its boiling temperature is 36.06° C., thus facilitating its evaporation. Moreover, it is aprotic, which means that it does not have acid hydrogen (hydrogen bound to a heteroatom such as an oxygen or nitrogen atom) capable of reacting with the siloxane functions (Si—O—Si functions of the PDMS). Protic solvents such as water or ethanol lead to gelation of the polydimethylsiloxane.

The microcolumn used for the tests has a rectangular cross-section. Given that the desired PDMS thickness is 200 nm and that the microcolumn has a depth of 200 µm and a width of 150 µm, the ratio $V_{PDMS}/V_{pentane}$ was estimated at 0.47%.

To compare the concentration of the PDMS solution used for the microcolumn with that commonly used in capillary columns, a calculation was performed by approximating the value of the internal diameter to that of the depth of the microcolumn in the equation above. For a depth of 200 µm, the ratio $V_{PDMS}/V_{pentane}$ was estimated at 0.4%. This value is therefore consistent with that calculated above.

To prepare the solution, this volume ratio is converted into a mass ratio: given that ρ=m/V, wherein ρ is the density of the compound, m is the mass and V is the volume, the mass ratio is:

$$\frac{m_{PDMS}}{m_{pentane}} = \frac{\rho_{PDMS}}{\rho_{pentane}} \times \frac{V_{PDMS}}{\rho V_{pentane}} = \frac{1.1}{0.63} \times 0.0047 = 0.0082$$

The mass ratio between PDMS and pentane is therefore 0.82%.

Step 2: Column Packing

This step consists of entirely packing the microcolumn with solution. Thus, the solution of PDMS diluted in the solvent is injected into the microcolumn by means of a syringe driver. Valves are installed at each end of the column in order to make it possible to easily control the opening and closing of the channel.

During packing, the two valves are open and the solution therefore circulates through the column. Once the column has been completely packed, the outlet valves, then the inlet valves, are successively closed. The column can thus be disconnected from the syringe driver. Before the column is connected to the vacuum pump for the solvent evaporation step, the access tube at the inlet of the microstructure is first disconnected in order to remove the solution contained inside the tube. The formation of a meniscus is observed at the inlet of the microstructure. This meniscus corresponds to the surface of the solution (PDMS diluted in pentane) where the evaporation of the solvent occurs. This will therefore make it possible to control the evaporation of the solvent.

The concentration of the solution also plays an important role in this step of the process. Indeed, in the case of inadequate dilution of the PDMS in the solvent, the wall of the meniscus forms a membrane not enabling the solvent to evaporate.

Step 3: Solvent Evaporation and Functionalization

Once the access tube at the inlet of the column has been reconnected, the vacuum pump can be connected to the column. A T-connection is inserted between the inlet valve and the pump in order to create a controlled leakage by a ring thus enabling the vacuum applied in the column to be controlled. The tightness at the connections between the assembly elements is an important parameter for ensuring continuity during the solvent evaporation process.

Once connected, the microcolumn is then placed in contact on a temperature-controlled hot plate enabling the temperature applied to the microstructure to be controlled.

When establishing contact with the microstructure, a slight movement of the meniscus is observed after the dilation of the solvent, due to the temperature change. Indeed, in a static packing process, the exterior heat is transferred to the meniscus, which enables the solvent to evaporate. The vapor of the solvent thus created, having a pressure higher than that of the column opening, passes through the column to the outlet.

In this process, the two main factors are the mass transfer (solvent vapor) toward the outlet and the heat transfer in the column. From Poiseulle's law, we get the following equation governing this physical phenomenon:

$$\frac{dV}{dt} = \frac{\pi d_c^4 (P^2 - P_0^2)}{256 L \eta_v P_{atm}}$$

wherein dV/dt is the solvent evaporation rate, P and $P_0$ are respectively the pressures at the meniscus and at the column outlet, $\eta_v$ is the viscosity of the solvent vapor. L is the distance between the meniscus and the column outlet, $P_{atm}$ is the atmospheric pressure and dc is the internal diameter of the column.

This equation makes it possible to demonstrate that the rate of evaporation of the solvent through the column is proportional to the term $P_2-P_0^2$ and inversely proportional to L. From the above equation, the following equation governing the packing rate is obtained:

$$\frac{dL}{dt} = \frac{273,16 d_c^2 (P^2 - P_0^2) M}{64.22400 T_c L \eta_v d_1 P_{atm}}$$

wherein dL/dt is the packing rate, M is the molar mass of the solvent, Tc is the packing temperature and d1 is the density of the solvent.

In a conventional static packing process, P is generally low and therefore the packing rate dL/dt is also low, in particular when the column to be filled is long or when its internal diameter is small. When a high packing temperature is used, the term $P_2-P_0^2$ can be high in spite of the fact that $P_0$ is also high. However, the use of a high temperature leads to a difference between the vapor tension $P_1$, equilibrium pressure between the liquid phase and the vapor phase of the solution, and P the pressure at the meniscus which will be higher. This phenomenon may increase the formation of bubbles, leading to a non-homogeneous functionalization of the column.

To increase the packing rate, a vacuum pump is connected at the column outlet. It makes it possible to reduce the value of $P_0$, thus promoting the mass transfer.

The initial conditions of the evaporation process are therefore the following: the vacuum pump (off) is connected to the inlet valve (closed) with the insertion of the control ring. The outlet valve is also closed. In a first stage, the pump is turned on with the control ring open so as to create a leakage. The inlet valve is then opened and the control ring is closed progressively in order to create a progressive vacuum in the column. A measurement of the vacuum is taken upstream of the inlet valve.

In our case, the evaporation of the solvent begins for a vacuum of around 0.2 bars and the temperature of the column is kept at 33° C. The progression of the meniscus, formed by the evaporation of the solvent, enables the progression of the deposition to be monitored. The meniscus therefore moves in the column from the inlet to the outlet.

The evaporation process lasts around 15 min, i.e. a rate of around 0.5 cm/s$^{-1}$. Once the meniscus reaches the column outlet, the vacuum is maintained for several minutes in order to enable the solvent contained in the outlet tube to evaporate. The vacuum is then progressively broken by means of the control ring.

The final step for functionalizing the microcolumn consists of placing the column in an oven at 80° C. for 2 hours in order to cross-link the PDMS layer deposited on the walls.

It is difficult to control the environmental parameters of temperature and vacuum applied to the microcolumn in the solvent evaporation process. Indeed, an inadequate temperature (below 31° C.) does not enable the solvent to evaporate, while an excessive temperature (above 35° C., i.e. around the boiling temperature of the solvent) causes a discontinuity in the evolution of the evaporation process through the column. The choice of a temperature of 33° C. was therefore made; however, the evaporation process remains sensitive to temperature.

The use of a controlled vacuum makes it possible to overcome this problem. Indeed, even if finding the appropriate temperature remains difficult, once the temperature of the microstructure has been stabilized, the management of the vacuum applied in the column makes it possible to control the solvent evaporation rate. A progressive increase in the vacuum thus makes it possible, on the one hand, to start the evaporation process (0.2 bars in this embodiment) and, on the other hand, to control the rate thereof (the greater the vacuum, the more the evaporation rate increases).

7.3.B Concentration Microstructure

The development of fungal contamination indices made it possible to identify Tenax TA, Tx, as a suitable adsorbent for trapping the molecules selected for fungal detection. This material is available in the form of grains of which the size was selected by means of a sieve in order to obtain diameters between 50 and 100 μm.

As the material is in grain form, it is therefore diluted in a solvent so as to be capable of being introduced into the microstructure by means of a syringe driver. The packing process for the concentration microstructure is less complex than for the functionalization of the microcolumn. Nevertheless, a phase of optimizing the functionalization of the microstructure by inserting Tenax grains into the device is preferable. The dilution and insertion rate parameters must in particular be defined in order to avoid risks of clogging of the structure access channel or destructurization of the microstructure.

The solvent used for functionalization of the concentration microstructure is ethanol. For the dilution parameter, the ratio between the Tenax volume and the ethanol volume ($V_{Tenax}/V_{Ethanol}$) is estimated at between 1 and 2%.

The concentration microstructure packing process therefore consists of injecting, via the syringe driver, the Tenax grains diluted in ethanol. A magnet, inserted into the syringe, coupled with the micro-agitator, makes it possible to keep the grains in the solvent in suspension. This makes it possible to overcome the problem of sedimentation of the Tenax grains at the bottom of the syringe. The grains transported by the solvent are thus injected one after another into the structure. The microstructure, in the vertical position, enables the grains to flow in the structure toward the outlet. The presence of the grid consisting of micropillars at the outlet of the structure then enables the grains to be filtered.

The use of a syringe driver makes it possible to control the packing rate and therefore to control the injection of the grains into the structure via the access channel. An excessive packing rate may, however, lead to the partial destruction of the walls forming the channels or to the formation of a crack on the back face of the structure.

The choice of a flow rate of 250 $\mu L/min^{-1}$ for the packing of the microstructure was made. This makes it possible to avoid, on the one hand, the clogging of the access channel by the grains injected into the structure, and, on the other hand, subjecting the microstructure to excessive stress, in particular at the end of the packing of the structure.

Once the microstructure has been completely packed, it is placed in the oven at 100° C. for 2 hours in order to remove the residual traces of solvent, then conditioned for two hours at 140° C. with a passage of filtered air through the structure.

7.4 Process for Producing the Detection Module

The data acquisition system, used in tests on the conductive polymer sensors, does not enable integration for the production of a fungal VOC analysis microchain. From this perspective, a detection module, based on the polymer matrix comprising the core of the acquisition system, was produced. Thus, the detection module is comprised of 4 pairs of interdigital electrodes for the depositions of polymer layers, and a stainless steel chamber enabling the polymer layers to be confined and the air to pass.

7.4.A Interdigital Electrodes

The card used previously in the acquisition does not make it possible to produce deposits simply and precisely.

On the one hand, its configuration and the method for depositing the different polymers require the same polymer to be deposited on all of the electrodes.

Indeed, successive depositions of other polymers or electrolytes as well as chemical doping (diiodine vapor) alter the previous deposits and do not therefore enable the mechanism of interaction uniquely between the VOC and the polymer to be understood. Moreover, the configuration of the electrodes used does not enable the deposition area of the polymer between the two electrodes to be controlled.

Figure 6:
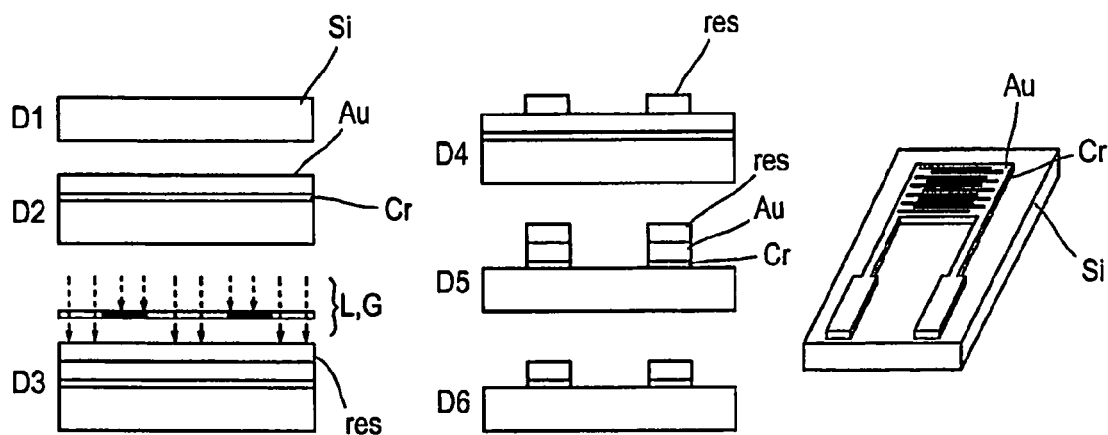
FIG. 6: a diagrammatic representation of the process for producing interdigital electrodes of the detection module.

Independent "chips" consisting of a single pair of interdigital electrodes were thus developed in order to overcome these disadvantages. As for the previous card, the electrodes are made of gold with a chromium attachment layer. The production process is presented in FIG. 6.

Step D1: Cleaning of the Wafer

The cleaning is identical to that used for the production of the previous modules.

Step D2: The Deposition of Chromium and Gold Layers

For the production of electrodes, the process consists of successively homogeneously depositing the chromium attachment layer over a thickness of 500 Å (deposition time 1 min 15 s), then the gold layer on a thickness of 10,000 Å (deposition time 10 min). The depositions are performed by cathode sputtering at ambient temperature (24° C.) in an argon plasma.

The next steps consist of defining the etching areas for the production of patterns. These steps therefore comprise a traditional UV photolithography phase, then wet etching of the chromium and gold layers.

Steps D3 and D4: Definition of Etching Areas

Once the layers have been deposited, the process consists of performing a traditional photolithography step enabling interdigital areas to be produced.

Figure 7:
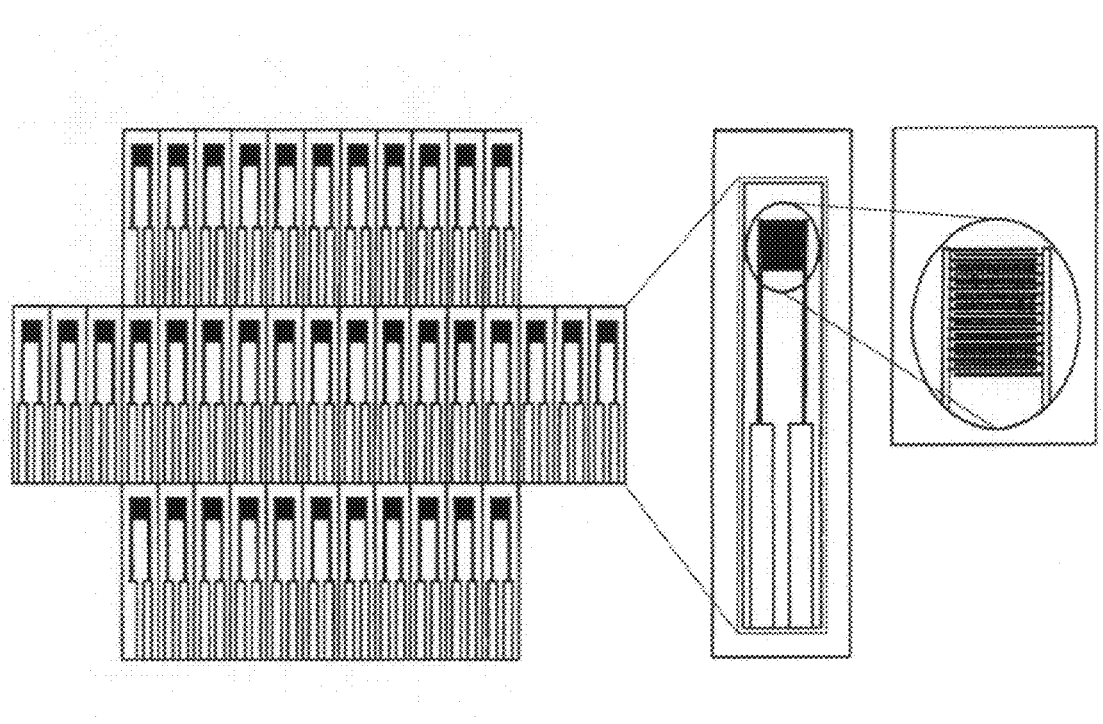
FIG. 7: a representation of the mask for the production of chips containing interdigital electrodes of the detection module.

Step D3 therefore consists of depositing a photosensitive resin layer (positive PFR resin 7790) using a whirler. The desired thickness is 1.2 µm (rotation speed of 4500 $rpm^{-1}$, acceleration of 2000 $rpm^{-2}$ for 30 s). The annealing of the resin is performed on a hot plate at 110° C. for 3 min. The photolithography step is then performed with a resin exposure time set at 10 s and a lamp power of 345 W. An image of the mask used during the exposure is presented in FIG. 7. This figure shows, from left to right, a set of chips, then one chip and finally an interdigital electrode.

The geometric characteristics used for the production of the chips containing an interdigital electrode pair are indicated in table 10.

TABLE 10

| Geometric characteristics (in µm) of the electrodes | | | | | | | | |
|---|---|---|---|---|---|---|---|---|
| Card | | Contact | | | Interdigital electrodes | | | |
| length | width | length | width | step | length | width | step | number |
| 26000 | 5080 | 12000 | 1580 | 2540 | 2500 | 60 | 240 | 13 |

Step D4 then consists of developing the resin thus forming the patterns etched subsequently. The wafer is therefore immersed in the developer bath (PRC 238) for 1 min 10 s. The wafer developed is then rinsed with deionized water for 3 min and dried before the second post-development annealing, thus enabling the resin to be completely hardened. This annealing step is performed in an oven at 100° C. for 15 min. The wafer is moreover cleaned with an O2 plasma in order to remove the resin residues (in particular at the bottom of the etched holes) after the development and improve the sharpness of the holes in the resin.

Step D5: Etching of Chromium and Gold Layers

The etchings of the gold and then the chromium are performed in chemical solutions comprised of acids. The solutions are kept at a temperature of 30° C.

The first bath is performed in a solution enabling the gold layer to be etched. The etching is visually checked until the entire gold layer has been removed in the areas defined by the resin. The wafer is then rinsed in deionized water.

The second bath is performed in a solution enabling the chromium layer to be etched. The etching is visually checked until the entire chromium layer has been removed in the areas defined by the resin. The wafer is then rinsed in deionized water.

A new very quick bath is then produced for the gold and the chromium etching at the interface of the two layers. The wafer is then rinsed in deionized water.

Step D6: Removal of the Resin Layer

Once the layers have been etched, the wafer is immersed in acetone in order to remove the remaining resin layer and the wafer then moves on to the rinser.

Once the card production process has been completed, a resin layer with a thickness of 3 µm is again deposited on the entire surface of the wafer so as to prevent particle deposits on the electrodes during the cutting of the different cards present on the wafer. The resin is then annealed at 110° C. for 1 min 30 s on a hot plate. Before using the cards to functionalize them with a conductive polymer, an acetone bath enables the protective resin layer to be removed.

7.4.B Confinement Chamber

As for the test system, the use of polymer sensors preferably involves the development of a chamber enabling the sensitive layers to be confined in order to be exposed only to air samples circulating in the system. The choice of stainless steel as the material for producing this chamber and the use of a Teflon seal (PTFE) makes it possible to limit the generation of background noise, as stainless steel and Teflon are non-emitting materials under the experimental conditions of this embodiment.

The confinement chamber is divided, for example, into two parts. A base part has four hollowed grooves, enabling the electrodes to be inserted. A stop enables the area for deposition of the polymer present on the electrode to be placed opposite the confinement "volumes" present on the cover part.

The cover part therefore consists of four confinement volumes linked to one another by a channel. These confinement volumes therefore make it possible to contain only the polymer deposition area and thus limit the dilution of the samples in excessive volumes. To ensure the tightness between the electrode and the confinement volumes, a Teflon seal is inserted in a groove between the two elements. The seal thus has four openings enabling the air samples present in the confinement volumes to be exposed to the sensitive layers of the electrodes.

Finally, the circulation of the air samples is ensured at the inlet and at the outlet of the chamber on the cover part by means of a NanoPort.

The dimensions and space between each sensor were defined so as to make it possible to use a pluggable connector with a step of 2.54 mm. This connector thus makes it possible to produce the connection between the sensors and an information processing card.

7.4.0 Information Processing

The sensors functionalized with a conductive polymer are placed in the confinement chamber in order to be capable of being used as a detection module of the analysis system. The principle of operation of these sensors is based on the variation in conductivity of the polymer induced by the adsorption of gaseous compounds at its surface. This adsorption is dependent on the affinity of the compound with the active site present in the polymer.

To convert this variation in conductivity into a measurable signal, the sensor is placed in an assembly enabling to measure a variation in electrical resistance called "Wheatstone bridge", P Wh. The principle of this assembly consists of balancing the two branches of the bridge by placing the sensor in one of the two branches. The variations in resistivity of the sensor produce an imbalance and the appearance of a voltage between the two branches of the bridge (see the diagram of FIGS. 10A and 10B).

In this assembly, dR represents the variation in resistivity of the sensor during the adsorption of the gaseous compounds at its surface. The value of the output voltage VS1 is defined by the elements of the assembly and is:

$$V_{S1} = \frac{VCC}{2} \frac{dR}{R}$$

wherein VCC is the voltage applied to the Wheatstone bridge assembly, P Wh.

When all of the resistances are equal (dR=0), the value of VS1 is equal to 0. When the resistivity of the sensor varies (dR≠0), then VS1 is the image of this variation and may be amplified by means of an amplifying assembly based on an operational amplifier, Ampli 1 (see the diagram of FIG. 10A).

This assembly makes it possible to amplify the voltage between $V_a$ and $V_b$ (i.e. $V_{S1}$) according to the value of the resistors comprising the assembly:

$$V_s = (V_a - V_b)G \text{ and}$$

$$G = 4 + \frac{60000}{R_1}$$

with $R_3$=30 kΩ and $R_4$=10 kΩ.

The output voltage of the assembly representing the variations in resistivity of the sensor then becomes:

$$V_s = V_{s1}G = \frac{dR}{R} \frac{VCC}{2}\left(4 + \frac{60000}{R_1}\right)$$

Figure 10A:
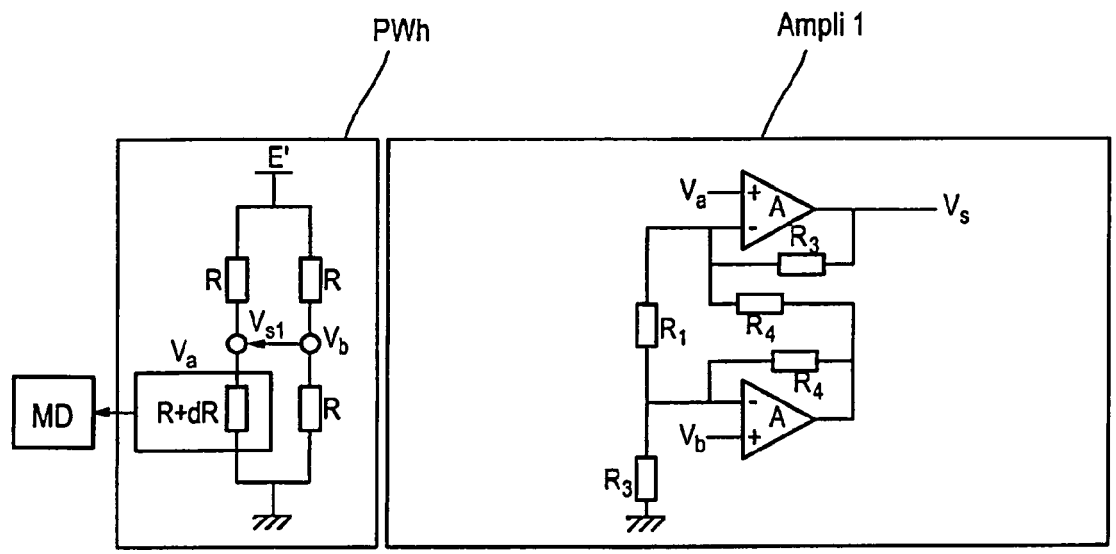
FIG. 10A: a "Wheatstone bridge" assembly and an amplification assembly for the processing of information of the sensors of the detection module.
Figure 10B:
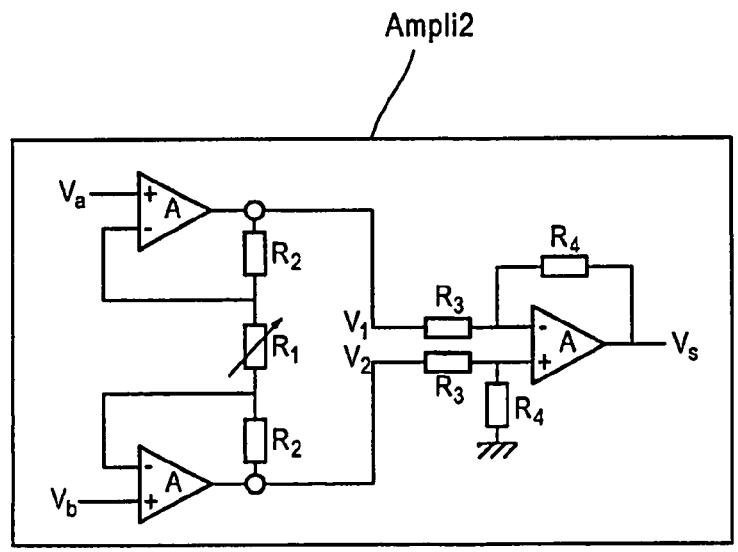
FIG. 10B: an amplification assembly for the processing of information of the sensors of the detection module.

From this perspective, a card enabling to process the information transmitted by the sensors was developed. It consists of associating a Wheatstone bridge with each sensor in order to convert the variation in resistivity into voltage and an amplifier assembly, Ampli 1 (FIG. 10A). Alternatively, the amplifier assembly, Ampli 2, of FIG. 10B may be used without going beyond the scope of the invention.

The diagram of the assembly developed under Cadence Allegro Design Entry represents one of the four assemblies used for the treatment of each of the sensors. A terminal combines the measurement signals of the different sensors and enables the connection with a measurement node so as to enable the user to receive the information transmitted. The references Cx (FIG. 13) designate the connection terminals of the processing card and the control card.

The four assemblies and the terminal together thus form a card for processing signals of different sensors. This assembly can then be integrated by means of the Allegro PCB Design tool in order to develop the card. This tool enables the placement and routing between the different components of the card by integrating all of the connections defined under Cadence Allegro Design Entry. The card for processing the signals transmitted by the sensors can then be produced.

7.5 Characterization of the Modules 7.5.A Sample Concentration Module

Figure 8:
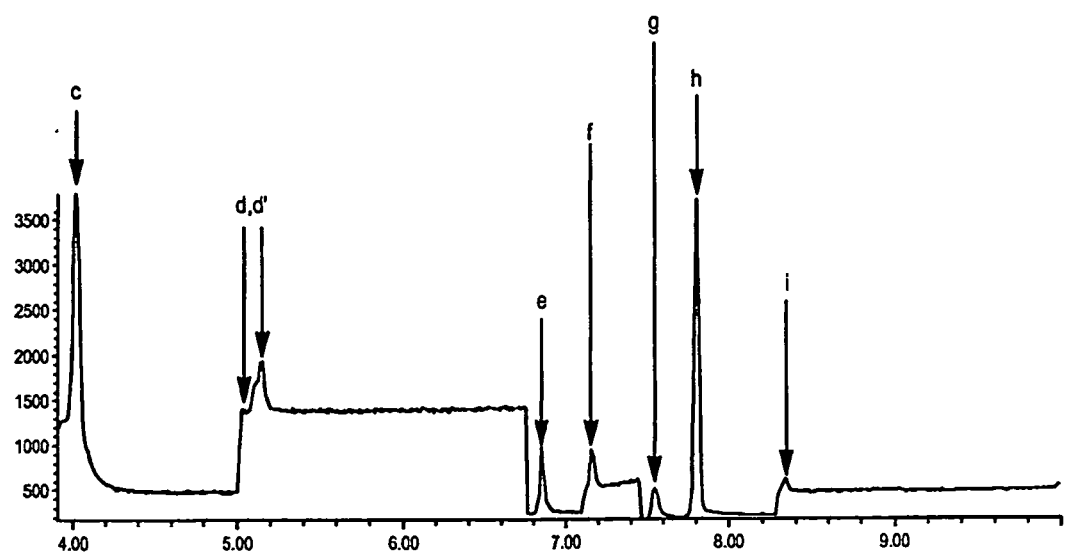
FIG. 8: a chromatogram of the emissions of the chamber containing 8 tracers (Hewlett Packard—SIM mode) for validation of the concentration module.

In reference to FIG. 8, the trapping and desorption of 8 tracers were validated by traditional chromatography. The 8 tracers were found with the climates contaminated by mold, but the concentrations observed are lower.

The peaks of FIG. 8 are as follows:
c: methylfuran; d: 2-methyl-1-butanol; d': 3-methyl-1-butanol; e: 4-heptanone; f: 3-heptanol; g: methoxybenzene; h: α-pinene; i: 1-octen-3-ol.

7.5.B Sample Separation Module

Figure 9:
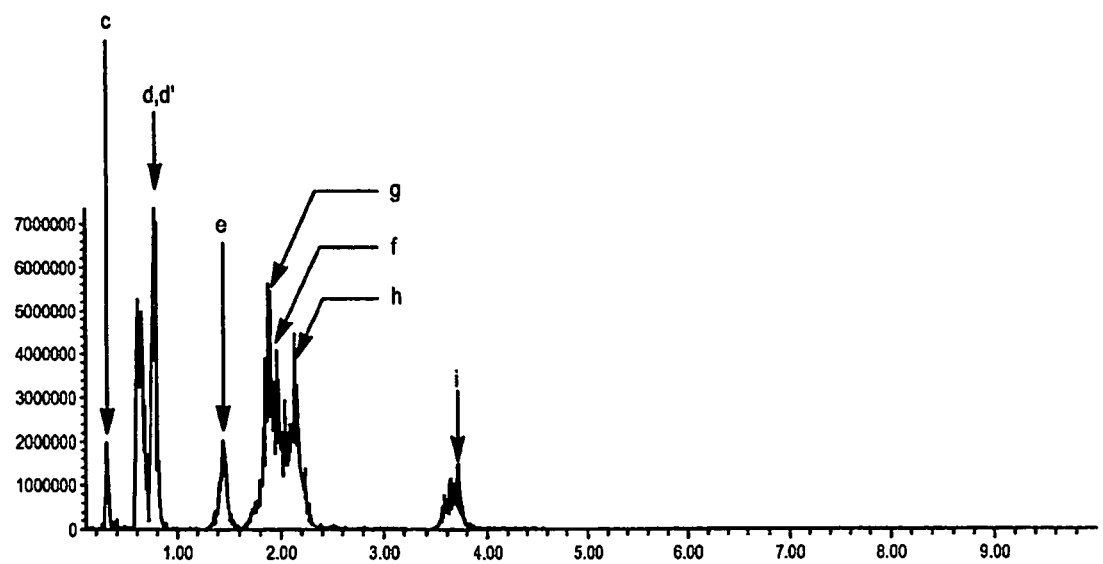
FIG. 9: a chromatogram obtained from the injection of 5 µL of the stock solution containing 8 tracers in ethanol (HP) for the validation of the separation module.

The separation module was also validated by chromatography and mass spectrometry. The chromatogram obtained from the 8 tracers in solution is presented in FIG. 9.

The microcolumn tested enabled the separation of 7 of the 8 tracers tested: 3-methyl-1-butanol and 2-methyl-1-butanol, which are isomers, were coeluted.

All of these tests also made it possible to find the conditions most suitable for separating the tracers (isothermal at 40° C. and helium flow rate at 0.5 ml/min$^{-1}$) and to considerably reduce the analysis time (around 10 min for the microcolumns by comparison with 1 h 30 s for a standard column). Thus, these tests made it possible to validate the separation module by showing that different retention times were obtained for the 11 tracers enabling the fungal contamination index to be calculated.

7.5.0 Detection Module

Tests were conducted on polypyrrole/sodium octane sulfonate (0.3 M) and PEDOT-PSS. These two sensitive layers were exposed to different volatile organic compounds (VOC). These tests were conducted according to the arrangements shown in FIGS. 10A and 10B.

Figure 10C:
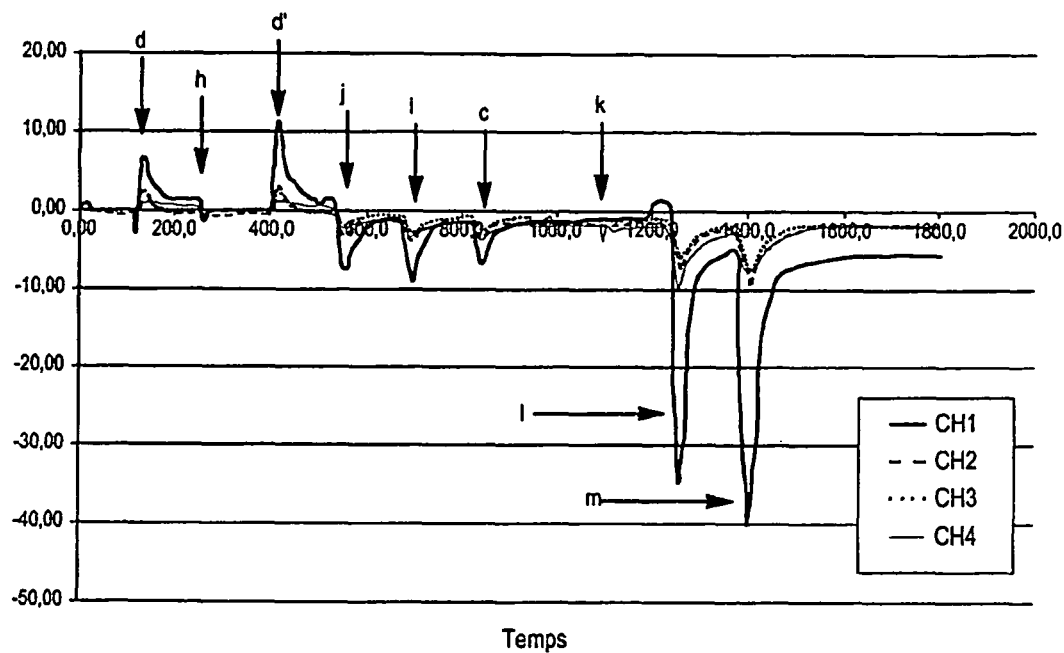
FIG. 10C: a diagram of the response of the Ppy/octane sulfonate film (0.3 M) to the 8 MVOCs in ethanol and water.

In the test shown in FIG. 10C, the 2 electronic conductive polymers are exposed to eight VOCs from the fungal contamination index, to distilled water (l) and ethanol (m). In general, references CH1 to CH4 designate different tests.

Negative fractional resistance differences were observed for six VOCs (alpha-pinene, anisole (j), 1-octen-3-ol, 2-methylfuran, 3-heptanol(k)), ethanol and water. However, positive fractional resistance differences were observed for two VOCs, 2-methyl-1-butanol and 3-methyl-1-butanol. These responses are similar for these 2 isomeric VOCs, which are primary alcohols. When the polymers are exposed to ethanol, which is a primary alcohol, a negative fractional resistance difference was observed. This is explained by the fact that it contains water.

Figure 10D:
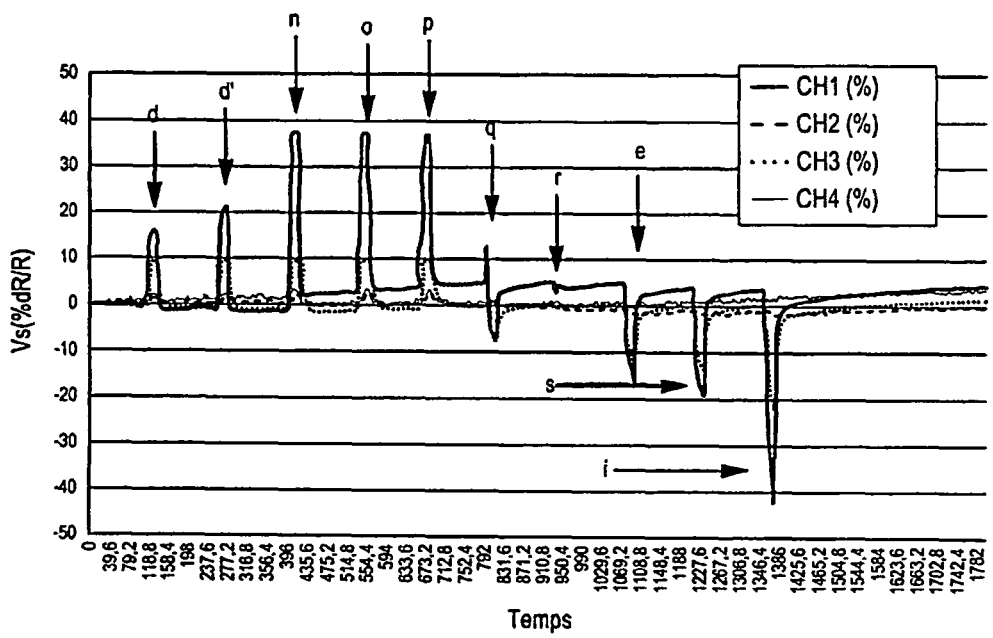
FIG. 10D: a diagram of the response of the Ppy/octane sulfonate (0.3 M) and PEDOT-PSS films.

To verify the selectivity to primary alcohols, the two sensitive layers were then exposed to a series of primary alcohols, 2-methyl-1-butanol, 3-methyl-1-butanol, 1-butanol (n), 1-pentanol (o) and 1-hexanol (p), to two alkanes, heptane (q) and octane (s), as well as to 3-heptanol (r), to 2-octen-3-ol and to 4-heptanone. Positive fractional resistance differences were observed for the primary alcohols. However, negative fractional resistance differences were observed for the other VOCs. The results are shown in FIG. 10D. In this figure, references CH1 and CH3 designate tests with PEDOT/PSS, and references CH2 and CH4 designate tests with OSS (0.3 M).

Figure 10E:
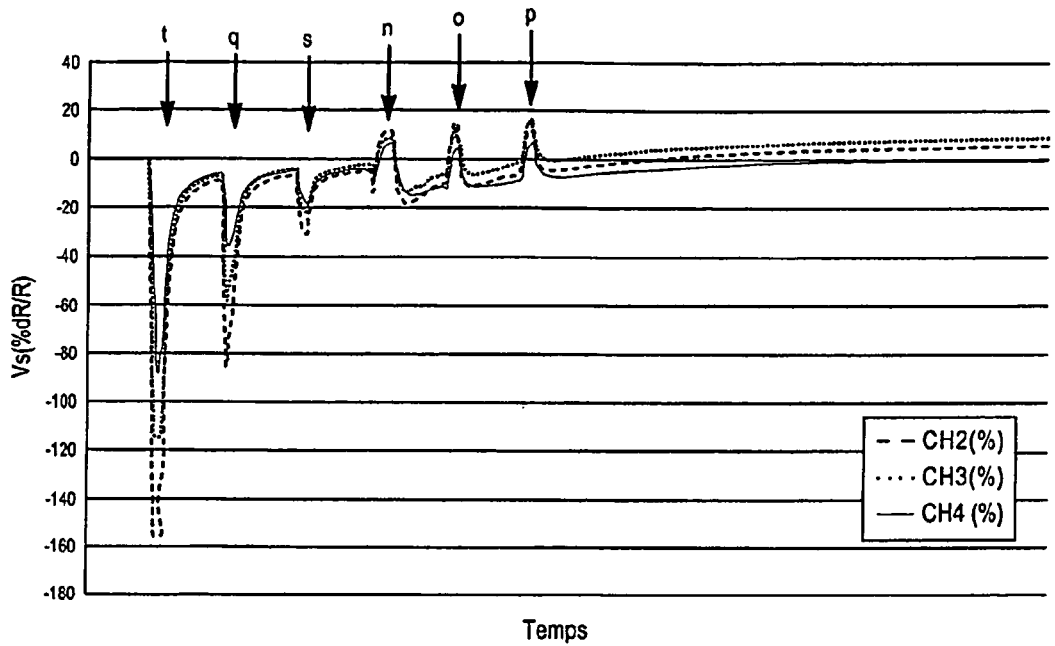
FIG. 10E: a diagram of the response of the PEDOT-PSS film.

The PEDOT-PSS was then exposed to a series of primary alcohols, 2-methyl-1-butanol, 3-methyl-1-butanol, 1-butanol, 1-pentanol and 1-hexanol, to three alkanes, pentane, heptane and octane. The results are illustrated in FIG. 10E.

During the exposure to alkanes, negative fractional resistance differences were observed.

Figure 10F:
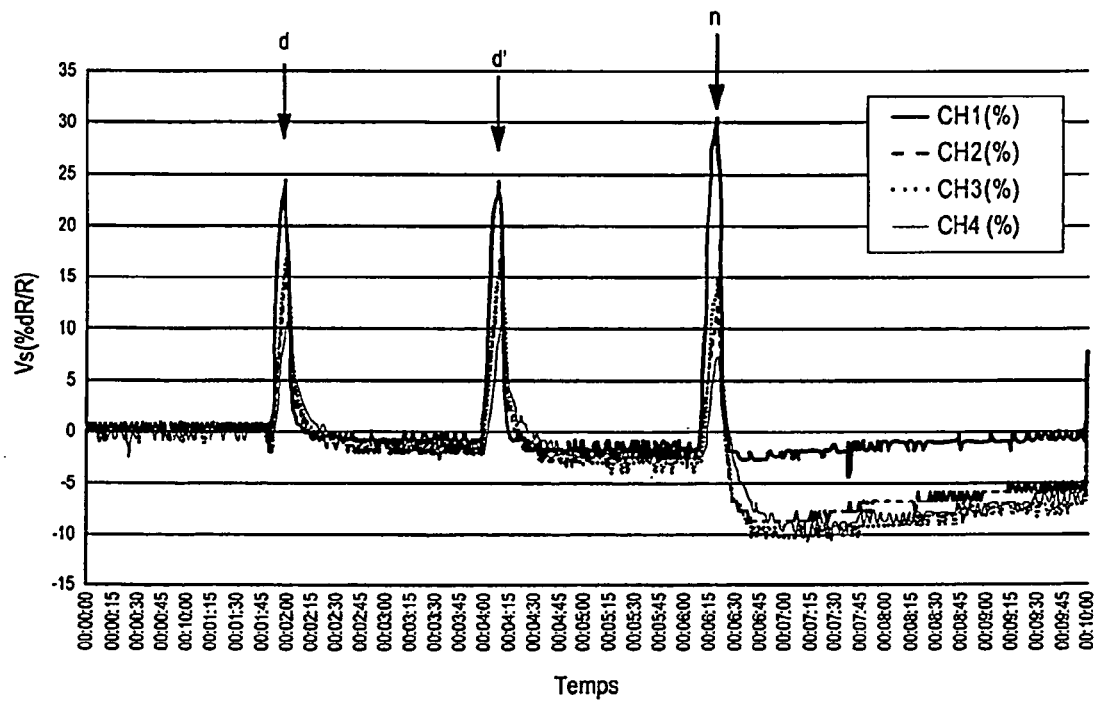
FIG. 10F: a diagram of the response of the PEDOT-PSS film for hindered alcohols.

This sensitive layer was then exposed to three primary alcohols with different hindrances. The results are shown in FIG. 10F.

It can be concluded from FIGS. 10C to 10F that when a primary alcohol is hindered, its fractional resistance difference decreases with respect to the unhindered alcohol.

The conductive polymers make it possible to go beyond the limits (modularity, specificity to polar compounds, energy consumption, etc.) of metal oxides or composite materials. Their chemical compositions are similar to those of the VOCs, thereby producing physical interactions between the polymer and the VOC. Moreover, their structures are modifiable, enabling materials with defined selectivities to be created in order to target the VOCs.

Example 7: Integration and Control of the System

Figure 11:
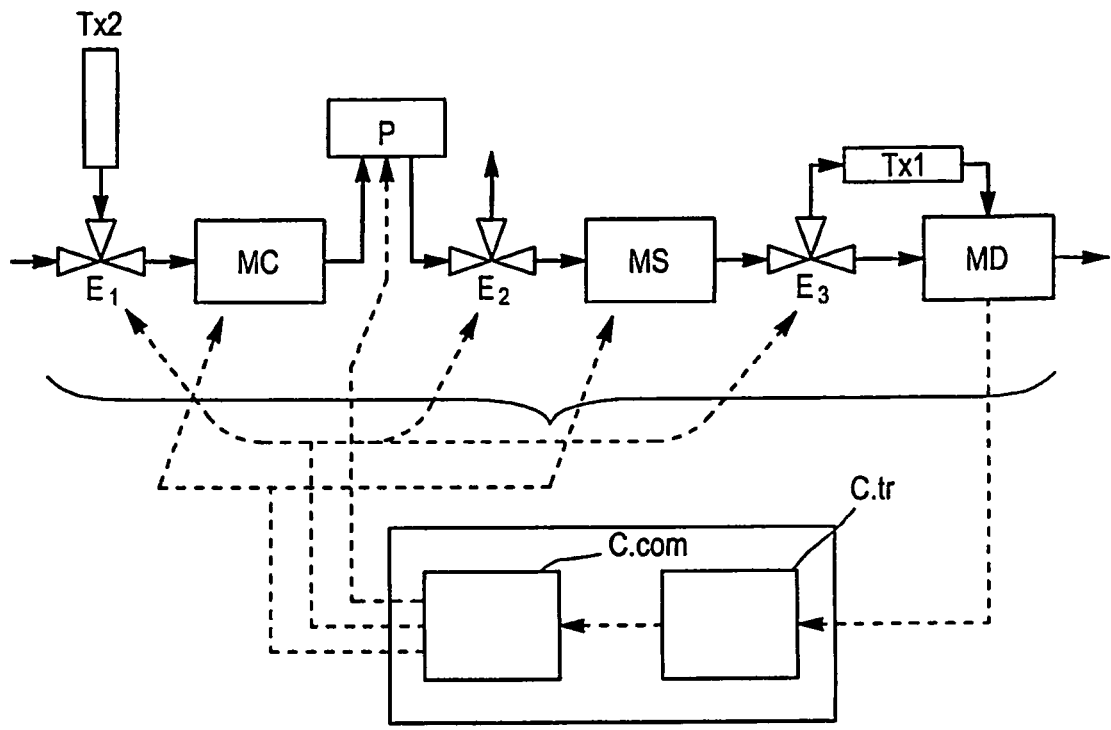
FIG. 11: a schematic diagram of the analysis system including the detection device and the control interface.

8. Control Interface of the Analysis System 8.1 Architecture of the Analysis System
8.1.A Principle of the Analysis System The schematic diagram of the system is shown in FIG. 11 and is therefore comprised of the three modules (the preconcentration module, the separation module and the detection module), a pump P and 3 solenoid valves E1, E2, E3.

The pump P selected is, for example, an eccentric membrane pump, sold by Scharzer Precision under reference SP 725 EC. The pump works under a direct current supply of between 0 and 24 V. The characteristics of the pump were chosen according to the head loss produced by the use of microchannels of between 1 and 2 bars.

During the concentration phase, the pump enables the sample to be collected by air circulation through the module. Thus, by a molecule accumulation process, after concentration, molecules contained in the air sample to be analyzed are retained in the microstructure. During the analysis phase, at the inlet of the system, a filter (activated carbon) enables by association with the pump, clean air circulation through the system thus serving as a vector gas.

The solenoid valves make it possible to choose the direction of the air flows during the analysis steps. Heating elements associated with a temperature regulator are also integrated in the system in order to enable the concentration and separation microstructures to be heated so as to enable the trapped molecules to be released.

The solenoid valves used in the system are miniature electromagnetic valves developed by Lee company.

Concerning the heating elements used for the concentration and separation modules, RC mica heaters produced by the MINCO company were chosen.

By way of illustration, the characteristics of the elements used for each of the two microstructures are indicated in table 11.

TABLE 11

Characteristics of mica heaters

| Dimensions (mm) | thickness (mm) | Resistance (Ohm) | effective surface (cm$^2$) |
|---|---|---|---|
| Concentrating heater | | | |
| 25.4 × 101.6 | 0.5 | 21.2 | 16.13 |
| Column heater | | | |
| 50.8 × 50.8 | 0.5 | 23.2 | 18.06 |

The system is controlled by means of a control card, C Com, enabling, on the one hand, to manage the controls of the solenoid valves, the temperature regulators and the pump, and, on the other hand, to collect the information transmitted by the sensors by means of a processing card, C Tr.

8.1.B Description of the Analysis Steps

Figure 12:
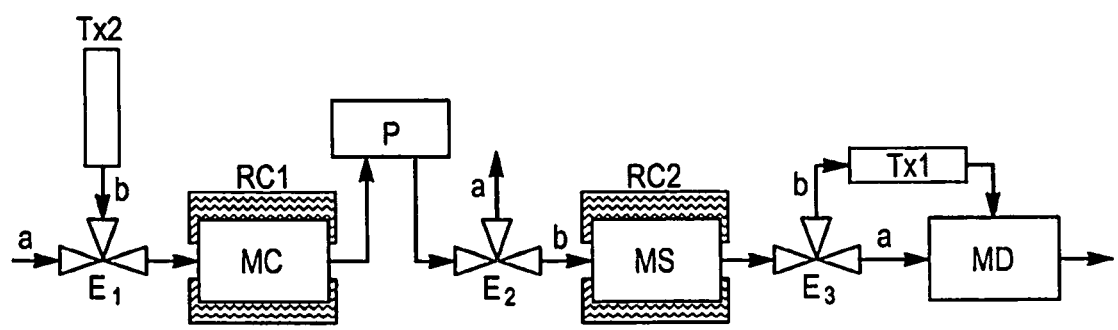
FIG. 12: a diagrammatic representation of the states of the elements of the analysis system.

The analysis of a sample is therefore broken down into two main steps identical to a traditional gas chromatography system, namely the concentration of the sample, then the analysis by separation. The use of pumps and solenoid valves makes it possible to direct the air flow through the modules by switching their states. A preferred illustration of the process shown in FIG. 12 associates the possible sates of the different elements comprising the system according to the analysis step performed. Four situations representing the analysis step can thus be defined: "inactive" 10, "concentration" 20, "molecule analysis" 40, and "sensor cleaning" 30.

An "inactive" state 10 of the system corresponds to the state of the system at the start and at the end of the analysis steps.

A "concentration" state 20 corresponds to the first step consisting of collecting the air to be analyzed through the concentration microstructure thus enabling the sample to be concentrated.

The "molecule analysis" 40 and "sensor cleaning" 30 states correspond to the two states taken by the system according to the presence or the absence of a molecule of interest.

Figure 14:
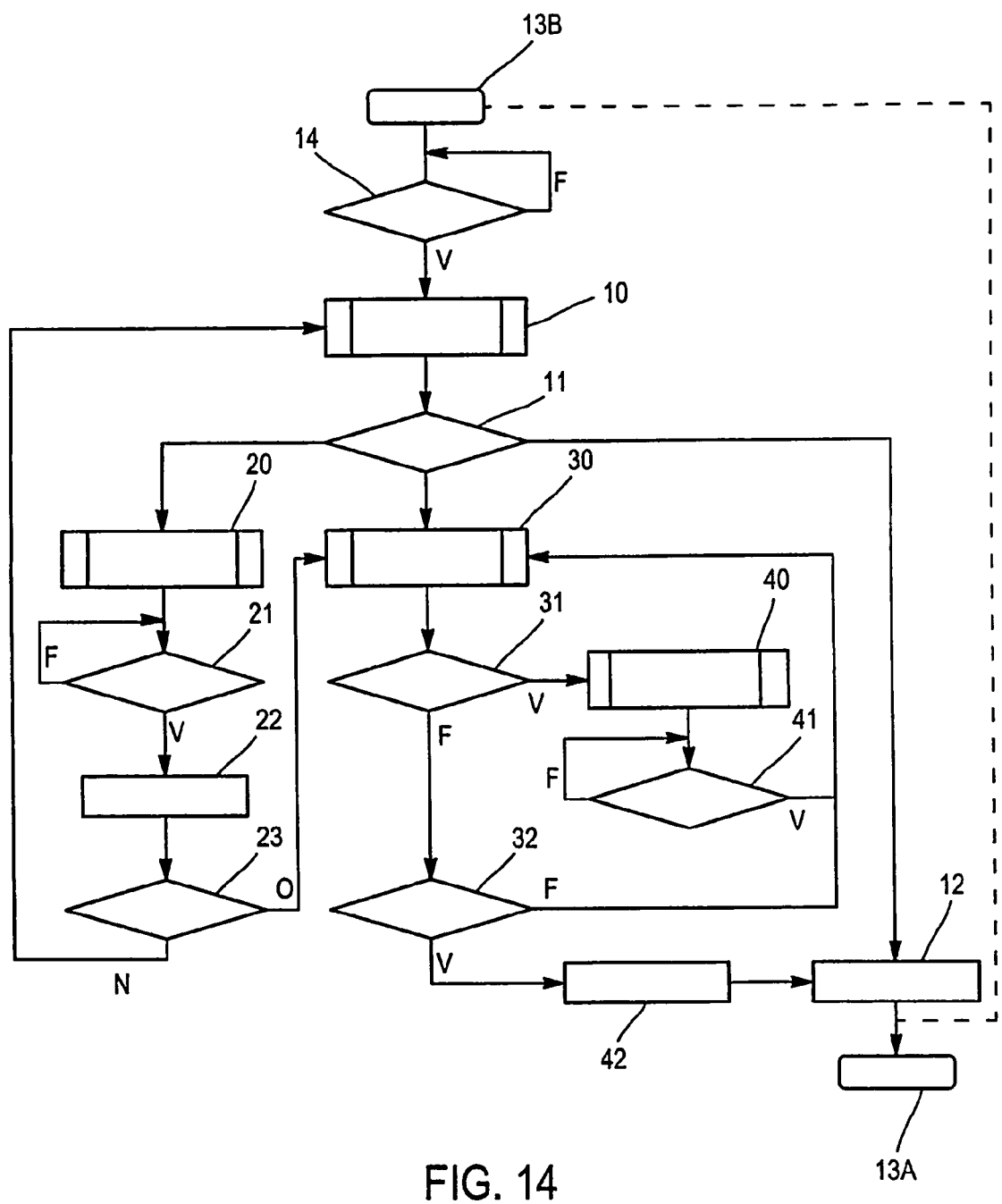
FIG. 14: a flow chart of the operation of the analysis system.

The other references of FIG. 14 are the following:
V: True; F: False; O: Yes; N: No; 13B: Start; 14: Init?; 11: Step choice?; 21: t=$t_{concen}$?; 23: Analysis?; 31: t=$t_{molecul}$?; 32: t=$t_{analysis}$?; 31: t=$t_{expo}$?; 42: analysis completed; 12: system stop; 13A: End.

The system enables the molecules of the sample to be separated with a retention time specific to the different molecules. At the outlet of the separation module, when the analysis time corresponds to the retention time of one of the molecules of interest, the system switches to the "molecule analysis" state for several seconds in order to direct the molecules to the detection module. When it is not time for a molecule to be analyzed to pass through, the system is kept in the "sensor cleaning" state thus enabling circulation of clean air (filtered by activated carbon) in the detection module.

Table 12 defines the states of the different elements of the system according to the analysis step performed. The pump state (P) is represented by an "On" state and an "Off" state when they are respectively on or off. The heating resistors, called RC1 for the concentration module and RC2 for the separation module, are also represented by an "On" state and an "Off" state when they are respectively powered or not. Finally, the solenoid valves (numbered 1 to 3 in FIG. 10) are represented by a state "a" or a state "b" according to the direction of the air flow chosen.

TABLE 12

States of the elements of the system according to the analysis step

| State of the system | Valve | | | Pump | Heating resistors | |
|---|---|---|---|---|---|---|
| | no. 1 | no. 2 | no. 3 | | RC1 | RC2 |
| Inactive | b | b | b | Off | Off | Off |
| Concentration | a | a | b | On | Off | Off |
| Sensor cleaning | b | b | b | On | On | On |
| Molecule analysis | b | b | a | On | On | On |

8.1.0 Description of Elements Constituting the Prototype

The system can use micro-elements such as pumps P, heating resistors RC and solenoid valves E. Seeking to obtain the most compact system possible, these elements were selected with a minimal bulk according to their performances in order to satisfy the constraints imposed by the system. These elements are commercially available at various specialists.

These elements are comprised of an etched laminar element contained between two mica layers for a thickness of 0.5 mm. These films can quickly reach high temperatures (up to 600° C.) with a homogenous temperature on the surface of the film. The microstructures to be heated are preferably placed in contact with the heater between two layers of insulating material (ceramic paper with a thickness of 3.2 mm) and mechanically held between two aluminum plates.

A temperature regulation system makes it possible to control the temperature applied to the microstructures. These three-way valves work by using a solenoid enabling magnetic locking of the valve toward one of the two inlet/outlet ports. The dimensions of these solenoid valves are designed to obtain a low internal volume (72 μL) in order to limit the dead volume.

8.2 Instruments for Controlling the System
8.2.A Generation of Control Signals

Figure 13:
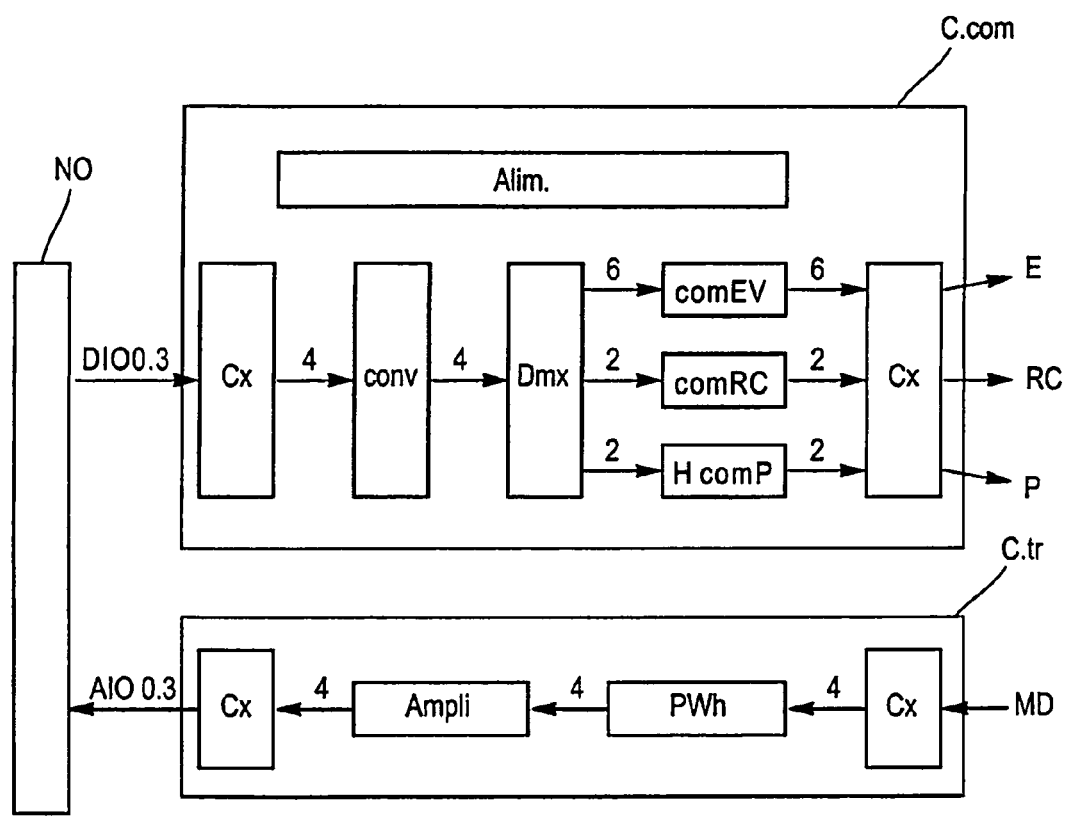
FIG. 13: a diagram of the control interface of the detection device.

As can be seen in FIG. 13, the operation of the device is managed by a control card, C. Com., associated with a processing card by means of a measurement node, No.

The control card receives information from the sensors and transmits it by means of a Wheatstone bridge assembly, Pwh, associated with an amplifier assembly, Ampli, provided in this case in the processing card.

A demultiplexing card, Dmx, is provided in the control card, associated with solenoid valve control relays (com EV), heating resistors (com RC), and an H-bridge for controlling the pump (H). This Dmx card makes it possible to generate different control signals from logic levels applied to each of the digital inputs of the measurement node. The control card preferably includes a voltage converter, cony, between the node, No, and the Dmx card.

Such a configuration enables the state of the different elements of the system to be managed in order to make it possible to control them via a computer.

The measurement node makes it possible to transmit the system state information sent by the user. The measurement node in this case offers 4 analog inputs 4A±10 V and 4 bidirectional digital inputs 4N. The control card is therefore designed so that it is possible to generate different states of the system by means of 4 digital input bits 4N (DIO 0 to DIO 3) of the measurement node in writing mode. The information transmitted by the sensors of the detection module is routed to the user by using the 4 analog inputs of the measurement node.

The diagram presented in FIG. 13 shows the generation part of the control signals, used to design the control card.

The control signals therefore generate voltages that make it possible to validate the application of a control voltage for the different elements by using relays, com. These components therefore function as switches controlled by the signals of the demultiplexing card.

As the solenoid valves are controlled by the polarity of the voltage applied, two relays are preferably used to control them: one relay to generate a positive polarity, the other to generate a negative polarity. During the decoding by the Dmx card, the use of 2 complementary control signals is therefore preferred for each of the solenoid valves (i.e. 8 signals).

The H-bridge, H com P, is preferred for the control of the pumps so as to be capable of using higher currents than for the solenoid valves.

8.2.0 Card Design

The power supply and voltage control of the elements comprising the card are traditional. This aspect is illustrated by the reference Alim.

The control card developed is in this case a two-sided card combining the different parts developed earlier.

On the basis of the 4 digital inputs of the measurement node (control bus), the Dmx card therefore makes it possible to generate up to 16 control signals (data bus) after demultiplexing. This thus makes it possible to control up to 4 pumps, 4, solenoid valves and 2 heating resistors. A decoding table can thus be programmed in the Dmx card according to the different values capable of being used by the control bus.

The decoding table is therefore simply comprised of the 4-bit control bus (DIO 0, DIO 1, DIO 2 and DIO 3) and the data bus comprised, for example, of 8 signals for controlling 4 solenoid valves (6 signals used for 3 solenoid valves), 6 signals for controlling 4 pumps (2 signals used for 1 pump) and 2 signals for controlling the heating resistors (FIG. 11).

rate of heating of the separation module in all-or-nothing mode. The state changes of the input DIO 2, and therefore of the module heating control are defined by a squarewave signal of which the cyclic ratio makes it possible to virtually create a controlled temperature ramp.

The control of a solenoid valve is performed by using two complementary relays so as to be capable of generating a control state according to the relay actuated. A control pulse is preferable in order to cause each of the solenoid valves to switch according to the polarity applied to the control inputs.

When the system changes states, a relay is therefore activated in order to apply a polarity at the control input of each of the solenoid valves.

Thus, table 13 shows the control table defined in order to control all of the elements of the system according to the analysis steps.

TABLE 13

| | | | | | | | | | | |
|---|---|---|---|---|---|---|---|---|---|---|
| | | | | System control table | | | | | | |
| Control bus | | | | State of the | Valve | | | | Heating resistors | |
| DIO 0 | DIO 1 | DIO 2 | DIO 3 | system | no. 1 | no. 2 | no. 3 | Pump | RC1 | RC2 |
| 0 | 0 | 0 | 0 | Inactive | −12 V | −12 V | −12 V | Off | Off | Off |
| 1 | 0 | 0 | 0 | Concentration | +12 V | +12 V | −12 V | On | Off | Off |
| 0 | 1 | 0 | 0 | Sensor cleaning | −12 V | −12 V | −12 V | On | On | X |
| 1 | 1 | 0 | 0 | Molecule analysis | −12 V | −12 V | +12 V | On | On | X |
| X | X | 0 | X | RC2 Heating control | X | X | X | X | X | Off |
| X | X | 1 | X | | X | X | X | X | X | On |
| X | X | X | 0 | Solenoid valve sleep control | +/−12 V | +/−12 V | +/−12 V | X | X | X |
| X | X | X | 1 | | 0 V | 0 V | 0 V | X | X | X |

* an X corresponds to any state of the signal.

8.3 User Interface

The programming of the demultiplexing card makes it possible to define the synchronization of the analysis by a change in state of the system by acting on the value of the control bus comprised of the 4 digital inputs of the system and enables a graphic display of the state of the different elements of the system, with the physical behavior being managed by the control card.

The flow chart is organized around the 4 possible states of the system ("inactive" 10, "concentration" 20, "molecule analysis" 40 and "sensor cleaning" 30) described above and generated by the two digital input bits DIO 0 and DIO 1. In the "sub-programs" corresponding to each of these states, two actions are performed: the state of the digital inputs of the control bus is transmitted to the measurement node and the values corresponding to the state of the elements of the system are assigned to the graphic objects representing them. The process and the flow chart are described in greater detail in part 8.3.B below.

As the digital inputs DIO 2 and DIO 3 are not used to define a state of the system, they make it possible to control the temperature regulation of the microcolumn and the to put the solenoid valve control signals in sleep mode.

The heating resistors are used in the analysis phase in order to release the molecules trapped in the preconcentration module and regulate the temperature of the separation module. In addition, if the heating of the preconcentration module does not require controlled regulation, as it must be produced as quickly as possible, the temperature regulation of the separation module may influence the molecule retention time. The digital input DIO 2 not being used to define an analysis phase of the system, it was used to control the 8.3.B Design of the User Interface The state of the elements of the system (valves, pumps and heating resistors) according to the different steps is indicated in table 13. The graphic display objects of these elements are therefore assigned by binary values enabling their changes over the different phases of the analysis to be observed.

The different input parameters of the system found in the flow chart make it possible to define the synchronization of the analysis steps.

The first two parameters therefore concern the sample collection time ($t_{concen}$) during the sample concentration phase and the time needed for the sample analysis ($t_{analysis}$). These two parameters can be adjusted by the user by means of control buttons on the user interface.

The next parameter concerns the management of the system during the sample analysis. Indeed, during this phase, the system may be in two states: the "sensor cleaning" state and the "molecule analysis" state. During the initialization phase, the system makes it possible to define the number of molecules that will be analyzed by associating them with a retention time ($t_{molecul}$) and an exposure time ($t_{expo}$), i.e. the time at which the system makes it possible to send the molecules retained to the detection module.

This data is indicated in a table and the comparison between the chronometer associated with the sample analysis time and the molecule retention times makes it possible to switch the system to the "molecule analysis" state during the exposure time associated with the molecule.

9. Characterization of the Analysis System

9.1 Characterization of Flow Rates

The pump makes it possible to obtain relatively high flow rates when it operates under vacuum. A plateau created by the use of micromodules is observed for a power supply voltage above 8 V. The maximum sample collection flow rate is therefore 7 mL/min. The power supply voltage used is 12 V, thus enabling the system to preserve an identical sample collection flow rate in the event of additional head losses produced by the collection of particles, for example.

9.2 Characterization of Temperature Ramps

Temperature ramps for each of the concentration and separation microstructures are also characterized. The maximum temperature adjusted by the set point of the regulators is 140° C.

Concerning the concentration microstructure, this set point temperature must preferably be obtained as quickly as possible in order to release the molecules retained in the shortest possible amount of time. The temperature ramps obtained for different power supply voltages, and therefore power injected to the heating resistor, were therefore characterized.

To obtain the temperature ramp as quickly as possible in this first prototype, the power supply voltage used is 20 V. As the heating resistor used for the concentration microstructure has a nominal resistance of 21.2Ω, the current consumed for a voltage of 20 V is around 0.94 A, i.e. a consumed power of 18.8 W.

The system was therefore designed so as to be capable of controlling the heating rate of the separation module by creating a temperature ramp by an all-or-nothing-mode power supply of the regulator.

For this, one of the digital inputs (DIO 2) makes it possible to directly control the control relay of the control relay of the heating resistor of the microcolumn (RC2).

The tests conducted when characterizing the microcolumn showed that a temperature of 40° C. is enough to separate the molecules of interest. The value of the cyclic ratio is therefore set at 10%.

To enable the release of molecules requiring a higher temperature and therefore the cleaning of the microcolumn, it must reach the maximum set point temperature.

As the heating resistor used for the separation microstructure has a nominal resistance of 23.2Ω, the current consumed for a voltage of 20 V is around 0.86 A, i.e. a consumed power of 17.2 W when the heating control is activated.

Numerous combinations can be envisaged without going beyond the scope of the invention; a person skilled in the art will select one or the other according to economic, ergonomic, dimensional or other constraints with which it is necessary to comply. For example, a person skilled in the art may configure a microcontroller instead of the control card and/or the processing card.

The invention claimed is:

1. Device for detecting fungal contamination in an interior environment, including:
   a preconcentration module configured to adsorb target molecules present in a fluid flow;
   a separation module including a chromatographic microcolumn fluidically connected downstream of the preconcentration module and configured to adsorb target molecules desorbed from the preconcentration module and separate the target molecules from one another;
   a detection module including a sensor matrix fluidically connected downstream of the separation module so that the detection module is configured to receive separated target molecules desorbed from the separation module and detect presence or absence of the separated target molecules in the fluid flow;
   one or more means for filtering the fluid flow before the fluid flow reaches the detection module;
   at least one first solenoid valve fluidically connected upstream of the detection module between the separation module and the detection module, the at least one first solenoid valve configured so that:
      upon the condition that presence of at least one of the separated target molecules is detected in the fluid flow by the detection module, the at least one first solenoid valve maintains direction of the fluid flow toward the detection module bypassing the one or more means for filtering; and
      upon the condition that the target molecules are absent from the fluid flow, the at least one first solenoid valve directs the fluid flow through the one or more means for filtering, enabling the detection module to be cleaned; and
   at least one pump disposed between the preconcentration module and the separation module, the at least one pump generating the fluid flow.

2. Detection device according to claim 1, further comprising at least one second solenoid valve placed upstream of the separation module and between the preconcentration module and the separation module, the at least one second solenoid valve configured so that:
   upon the condition that presence of at least one of the separated target molecules is detected by the detection module or the fluid flow is filtered by the one or more means for filtering, the at least one second solenoid valve directs the fluid flow toward the separation module; and
   upon the condition that the targeted molecules are absent from the fluid flow, the at least one second solenoid valve directs the fluid flow outside the device.

3. Detection device according to claim 1, further comprising at least one third solenoid valve upstream of the preconcentration module, the at least one third solenoid valve configured so that:
   upon the condition that presence of at least one of the separated target molecules is detected by the detection module, the at least one third solenoid valve directs the fluid flow toward the preconcentration module; and
   upon the condition that the targeted molecules are absent from the fluid flow, the at least one third solenoid valve directs the fluid flow filtered by the one or more means for filtering, enabling the preconcentration module to be cleaned.

4. Detection device according to claim 1, wherein the one or more means for filtering includes an adsorbent polymer, based on 2,6-diphenylene.

5. Detection device according to claim 1, wherein at least one of the preconcentration or separation modules comprises an adsorbent polymer.

6. Detection device according to claim 5, wherein the adsorbent polymer comprises polymer beads, based on 2,6-diphenylene oxide, in the case of the preconcentration module, and polydimethylsiloxane (PDMS) in the case of the separation module, and the preconcentration and separation modules comprise heating resistors to desorb the target molecules.

7. Detection device according to claim 6, further comprising a control interface including a control card configured to control operation of the at least one first solenoid valve, the heating resistors, and the at least one pump.

8. Detection device according to claim 7, further comprising a processing card that connects the control interface to the detection module.

9. Detection device according to claim 8, wherein the control card and the detection module are configured to measure a difference in resistivity between the fluid flow containing the target molecules and the filtered fluid flow.

10. Detection device according to claim 1, wherein the sensor matrix of the detection module comprises a conductive polymer selected from the group consisting of PEDOT-PSS, dibromine bifluorene, polypyrrole doped with octane sulfonate, polypyrrole doped with lithium perchlorate and any other derivative of polypyrrole, polythiophene and polyaniline.

* * * * *